United States Patent
Rohner-Jeanrenaud et al.

(10) Patent No.: US 9,101,569 B2
(45) Date of Patent: Aug. 11, 2015

(54) METHODS FOR THE TREATMENT OF INSULIN RESISTANCE

(75) Inventors: Françoise Rohner-Jeanrenaud, Thonex (CH); Nicolas Deblon, Reignier (FR)

(73) Assignee: UNIVERSITE DE GENEVE, Geneva (CH)

(*) Notice: Subject to any disclaimer, the term of this patent is extended or adjusted under 35 U.S.C. 154(b) by 36 days.

(21) Appl. No.: 13/698,385

(22) PCT Filed: May 17, 2011

(86) PCT No.: PCT/IB2011/052156
§ 371 (c)(1),
(2), (4) Date: Nov. 16, 2012

(87) PCT Pub. No.: WO2011/145051
PCT Pub. Date: Nov. 24, 2011

(65) Prior Publication Data
US 2013/0085100 A1    Apr. 4, 2013

Related U.S. Application Data

(60) Provisional application No. 61/345,616, filed on May 18, 2010, provisional application No. 61/447,103, filed on Feb. 28, 2011.

(51) Int. Cl.
*A61K 38/11* (2006.01)
*A61K 45/06* (2006.01)

(52) U.S. Cl.
CPC ............ *A61K 38/11* (2013.01); *A61K 45/06* (2013.01)

(58) Field of Classification Search
None
See application file for complete search history.

(56) References Cited

U.S. PATENT DOCUMENTS 2,938,891 A    5/1960    Velluz et al.
3,076,797 A    2/1963    Velluz et al.

FOREIGN PATENT DOCUMENTS

| EP | 1 928 484 | 2/2010 |
|---|---|---|
| WO | WO 2003/016316 | 2/2003 |
| WO | WO 2004/072083 | 8/2004 |
| WO | WO 2004/078147 | 9/2004 |
| WO | WO 2005/023812 | 3/2005 |
| WO | WO 2007/050353 | 5/2007 |
| WO | WO 2008/008357 | 1/2008 |
| WO | WO 2008/042452 | 4/2008 |

OTHER PUBLICATIONS

Marazziti et al. Clinical Neuropsychiatry 3(5): 302-321, 2006.*
Gimpl et al. Eur. J. Pharmacol. 510: 9-16, 2005.*
Camerino, C. "Low Sympathetic Tone and Obese Phenotype in Oxytocin-deficient Mice" *Obesity*, 2009, pp. 980-984, vol. 17, XP-002658027.

(Continued)

*Primary Examiner* — Christine J Saoud
(74) *Attorney, Agent, or Firm* — Saliwanchik, Lloyd & Eisenschenk

(57) ABSTRACT

The present invention is directed to a derivative selected from oxytocin, an oxytocin derivative, and an oxytocin agonist useful for the treatment of a disorder selected from obesity and insulin resistance and related methods and pharmaceutical formulations. In particular, the invention relates to a derivative selected from oxytocin, an oxytocin derivative, and an oxytocin agonist useful in the treatment of metabolic syndrome.

11 Claims, 11 Drawing Sheets

(56) References Cited

OTHER PUBLICATIONS

Eckertova, M. et al. "Subchronic treatment of rats with oxytocin results in improved adipocyte differentiation and increased gene expression of factors involved in adipogenesis" *British Journal of Pharmacology*, 2011, pp. 452-463, vol. 162, XP-002658026.

Fabian, E. et al. "Inhibition of Lipolysis by Oxytocin and Vasopressin" *Acta Universitatis Carolinae. Medica. Monographia*, 1977, pp. 141-145, No. 77, Pt. 1, XP-009151733.

Gimpl, G. et al. "The Oxytocin Receptor System: Structure, Function, and Regulation" *Physiological Reviews*, Apr. 2001, pp. 629-683, vol. 81, No. 2, XP-002263271.

Hanif, K. et al. "Oxytocin Action, Mechanisms for Insulin-Like Activity in Isolated Rat Adipocytes" *Molecular Pharmacology*, Sep. 1982, pp. 381-388, vol. 22, No. 2, XP-009151676.

Muchmore, D.B. et al. "A Dual Mechanism of Action of Ocytocin in Rate Epididymal Fat Cells" *The Journal of Biological Chemistry*, Jan. 10, 1981, pp. 365-372, vol. 256, No. 1, XP-002658025.

Nishimori, K. et al. "New aspects of oxytocin receptor function revealed by knockout mice: sociosexual behavior and control of energy balance" *Progress in Brain Research*, Jan. 1, 2008, pp. 79-90, vol. 170, XP-009151673.

Deblon, N. et al. "Mechanisms of the Anti-Obesity Effects of Oxytocin in Diet-Induced Obese Rats" *PLos ONE*, Sep. 2011, pp. 1-13, vol. 6, Issue 9, e25565.

Takayanagi, Y. et al. "Oxytocin receptor-deficient mice developed late-onset obesity" *Neuroendocrinology*, Jun. 11, 2008, pp. 951-955, vol. 19, No. 9.

Defronzo, R.A. "Overview of Newer Agents: Where Treatment is Going" *The American Journal of Medicine*, 2010, p. S38-S48, vol. 123.

Written Opinion in International Application No. PCT/IB2011/052156, Sep. 16, 2011, pp. 1-9.

Stock, S. et al. "Elevated plasma levels of oxytocin in obese subjects before and after gastric banding" *Int J. Obes*, 1989, pp. 213-222, vol. 13, No. 2, abstract only.

Arletti, R. et al. "Influence of Oxytocin on Feeding Behavior in the Rat" *Peptides*, 1989, pp. 89-93, vol. 10.

Blevins, J. E. et al. "Evidence that paraventricular nucleus oxytocin neurons link hypothalamic leptin action to caudal brain stem nuclei controlling meal size" *Am J Physiol Regul Integr Comp Physiol*, 2004, pp. R87-R96, vol. 287.

Coiro, V. et al. "Oxytocin response in insulin-induced hypoglycemia in obese subjects before and after weight loss" *J. Endocrinol. Invest.*, 1998, pp. 125-128, vol. 11.

Dubuc, P. U. et al. "The Effects of Exercise and Food Restriction on Obesity and Diabetes in Young Ob/Ob Mice" *International Journal of Obesity*, 1984, pp. 271-278, vol. 8, No. 3.

Myers, M. G. et al. "Mechanisms of Leptin Action and Leptin Resistance" *Annu. Rev. Physiol.*, 2008, pp. 537-556, vol. 70.

Schwartz, M. W. et al. "Central nervous system control of food intake" *Nature*, Apr. 6, 2000, pp. 661-667, vol. 404.

Verty, A. N. A. et al. "Evidence for an interaction between $CB_1$ cannabinoid and oxytocin receptors in food and water intake" *Neuropharmacology*, 2004, pp. 593-603, vol. 47.

* cited by examiner

A

B

A

B

A

B

C

| Gene | Ascension Number | Forward primer sequence | Reverse primer sequence |
|---|---|---|---|
| Lpl | L03294 | 5'-GGCATACAGGTCAATTCCA (SEQ ID NO: 3) | 5'-CGTCGAACTTGGACAGATCCTT (SEQ ID NO: 4) |
| Acaca | J03808 | 5'-ACCTCAACCACTACGGCATGA (SEQ ID NO: 5) | 5'-AGGTGGTGTGAAGGCGTTGT (SEQ ID NO: 6) |
| Fasn | NM017332 | 5'-GGACATGGTCACAGACGATGAC (SEQ ID NO: 7) | 5'-CGTCGAACTTGGACAGATCCTT (SEQ ID NO: 8) |
| Dgat1 | NM053437 | 5'-GTTCAGCTCAGACAGCGGTTT (SEQ ID NO: 9) | 5'-CATCACCACGCACCAATTCA (SEQ ID NO: 10) |
| Pnpla2 | NM001108509 | 5'-GGCCATGATGGTGCCCTATA (SEQ ID NO: 11) | 5'-CCAACAAGCGGATGGTGAA (SEQ ID NO: 12) |
| Hsl | NM012859 | 5'-CGCCGACATGTCACAGTCAAT (SEQ ID NO: 13) | 5'-GAATTCCCGGATCGCAGAA (SEQ ID NO: 14) |
| PPAR-α | NM013196 | 5'-GTCCCTCGGAGAGG (SEQ ID NO: 15) | 5'-GGAAGCTGGAGAGA (SEQ ID NO: 16) |
| Acox1 | NM0173340 | 5'-CGACCTTGTTCGGGCAAGT (SEQ ID NO: 17) | 5'-TGAGAAGACCTTAACGACCACGTA (SEQ ID NO: 18) |
| Ehhadh | NM133606 | 5'-TCCCTGGCTTTCTACGTTCCT (SEQ ID NO: 19) | 5'-GATGGTGCGCTGCTCGAT (SEQ ID NO: 20) |
| Acadm | NM016986 | 5'-CGCCGGAACACGTACTTTG (SEQ ID NO: 21) | 5'-CGAGCTGGTTGGCAATATCTC (SEQ ID NO: 22) |
| Ucp3 | NM019354 | 5'-GGACAGCAGCCTGTATTGCA (SEQ ID NO: 23) | 5'-GGGTTGCACTTCGGAAGTTGT (SEQ ID NO: 24) |
| Scd1 | NM139192 | 5'-CCGTGGCTTTTCTTCTCTCA (SEQ ID NO: 25) | 5'-CTTTCCGCCCTTCTCTTTGA (SEQ ID NO: 26) |
| Oxt | NM012996 | 5'-CGCCTGCGACCCTGAGT (SEQ ID NO: 27) | 5'-AAGGAAGCGCCCTAAAGGTATC (SEQ ID NO: 28) |

Figure 9

METHODS FOR THE TREATMENT OF INSULIN RESISTANCE

This application is the U.S. national stage application of International Patent Application No. PCT/IB2011/052156, filed May 17, 2011, which claims the benefit of U.S. Provisional Patent Application No. 61/345,616, filed May 18, 2010 and U.S. Provisional Patent Application No. 61/447,103, filed Feb. 28, 2011.

The Sequence Listing for this application is labeled "Seq-List-replace.txt" which was created on Dec. 10, 2012 and is 7 KB. The entire contents of the sequence listing is incorporated herein by reference in its entirety.

FIELD OF THE INVENTION

The present invention relates to substances and compositions thereof useful in the treatment of obesity and/or insulin resistance. In particular, the invention relates to substances and compositions thereof useful in the treatment of metabolic syndrome.

BACKGROUND OF THE INVENTION

According to a world-wide estimate from the World Health Organization (WHO) for 2005, at least 400 millions of adults present excess body weight and most of them suffer from pathologies related to this overweight. The WHO estimates that by 2015, 2.3 billions of adults will suffer from overweight and that 700 millions of adults will be obese. Obesity is associated with increased circulating plasma levels of free fatty acids and triglycerides which contribute to insulin resistance in peripheral tissues like skeletal muscle. In obesity, adipose tissues are enlarged and present an altered secretion profile is for hormones, such as adipokines like leptin and adiponectin, playing a role in the control of body weight, insulin sensitivity, inflammation, angiogenesis, and lipid metabolism, as compared to healthy individuals.

It is known that excess body weight, and in particular adiposity, is directly associated with a reduction in insulin sensitivity, generally compensated by a further stimulation of pancreatic insulin secretion to prevent an increase in blood glucose levels. Therefore, increased adiposity, especially in the abdominal region, is known to be a strong risk factor for the development of insulin resistance which may then progress into type 2 diabetes. Increased peripheral insulin resistance, defined as a less effective response of tissues to insulin in terms of glucose uptake and inhibition of hepatic glucose production, leads first to β-cells having an initial attempt to override the increased insulin demand and then results in an alteration in their functional role and a decline in their number, a dysfunction leading to hyperglycaemia and characterizing type 2 diabetes.

Further, obesity is one of the major components of the metabolic syndrome, characterized as a cluster of syndromes including central obesity plus at least two other conditions selected from elevated serum triglycerides, low levels of high density cholesterol (HDL), elevated blood pressure and elevated fasting glucose due to insulin resistance. Metabolic syndrome patients are twice as likely to die from, and three times as likely to have, a heart attack or stroke compared with people without the syndrome. In addition, people with metabolic syndrome have a fivefold greater risk of developing type 2 diabetes. Over 60% of metabolic syndrome patients will progress to type II diabetes, 50% will develop a cardiovascular disease, over 35% will suffer an acute myocardial infarction, and up to 20% will suffer a stroke. It is estimated that around 20-25% of the world's adult population have the metabolic syndrome. Further, obesity is also known to be a strong risk factor for the development of further disorders such as some cancers.

Therefore, there is huge heath and economical needs for the development of new treatments for managing obesity and/or insulin resistance. There is a need as well for the development of treatments for metabolic syndrome as there is currently no treatment is available for this multi-component syndrome and this syndrome is the source of further disorders such as severe cardiovascular and diabetic complications.

Oxytocin (OT) is a neurohypophyseal hormone nonapeptide (Cys-Tyr-Ile-Gln-Asn-Cys-Pro-Leu-Gly (SEQ ID NO: 1)) synthesized both centrally and peripherally and exerting various physiological effects. Within the central nervous system (CNS), the OT gene is expressed in neurons of the hypothalamic paraventricular (PVN) and supraoptic nuclei (SON). The magnocellular OT neurons in these nuclei project to the neurohypophysis and are the major source of systemically released OT, whereas parvocellular OT neurons of the PVN project centrally. OT is synthesized peripherally in several organs, such as the ovary, testis, thymus, kidney and heart. Up to now, a single OT receptor (OTR) was cloned, which is expressed in various tissues, including adipose tissue. In keeping with such a wide distribution in its production and binding sites, OT was demonstrated to be implicated in several central and peripheral processes (Gimpl et al., 2001, Physiol. Rev., 81, 629-683). OT is currently used for stimulation of uterine contraction to induce labor, for the control of post-partum hemorrhage following delivery of placenta and for stimulation of lactation (Pitocin®, Parke-Davis, Morris Plains, N.J. and Syntocinon®, Novartis Pharmaceuticals, East Hanover, N.J.). Administration of OT has been reported to also increase female sexual response and to be beneficial in the treatment of male sexual dysfunction (Pfaus, 2009, *J. Sex Med. June*, 6, 1506-33).

SUMMARY OF THE INVENTION

The present invention relates to the unexpected finding that OT administration in a high fat diet-induced model of obesity induces a dose-dependent decreased body weight gain due to improved lipid metabolism, in particular increased lipolysis and fatty acid β-oxidation in adipose tissue, accompanied by improvements in glucose intolerance and insulin resistance, independently of food intake.

A first aspect of the invention provides a derivative selected from oxytocin, an oxytocin derivative and an oxytocin agonist for the repression or treatment of a disorder selected from obesity and insulin resistance.

A second aspect of the invention relates a use of a derivative selected from oxytocin, an oxytocin derivative and an oxytocin agonist for the preparation of a pharmaceutical is preparation for the treatment of a disorder selected from obesity and insulin resistance.

A third aspect of the invention relates to a method of treating or ameliorating a disease or a disorder selected from obesity and insulin resistance, said method comprising administering in a subject in need thereof a therapeutically effective amount of a derivative selected from oxytocin, an oxytocin derivative and an oxytocin agonist or a pharmaceutical formulation thereof.

A fourth aspect according to the invention relates to a pharmaceutical formulation comprising a derivative selected from oxytocin, an oxytocin derivative and an oxytocin agonist combined with at least one co-agent useful in the treatment of a disease or a disorder selected from obesity and insulin resistance, and at least one pharmaceutically acceptable carrier.

DESCRIPTION OF THE FIGURES

FIGS. 1-3: Values are mean±SEM of 6 to 7 animals per group. *$P<0.05$, **$P<0.01$ compared to controls.

FIG. 9 represents the primer sequences used for qPCR as described in Example 1.

DETAILED DESCRIPTION

Figure 1:
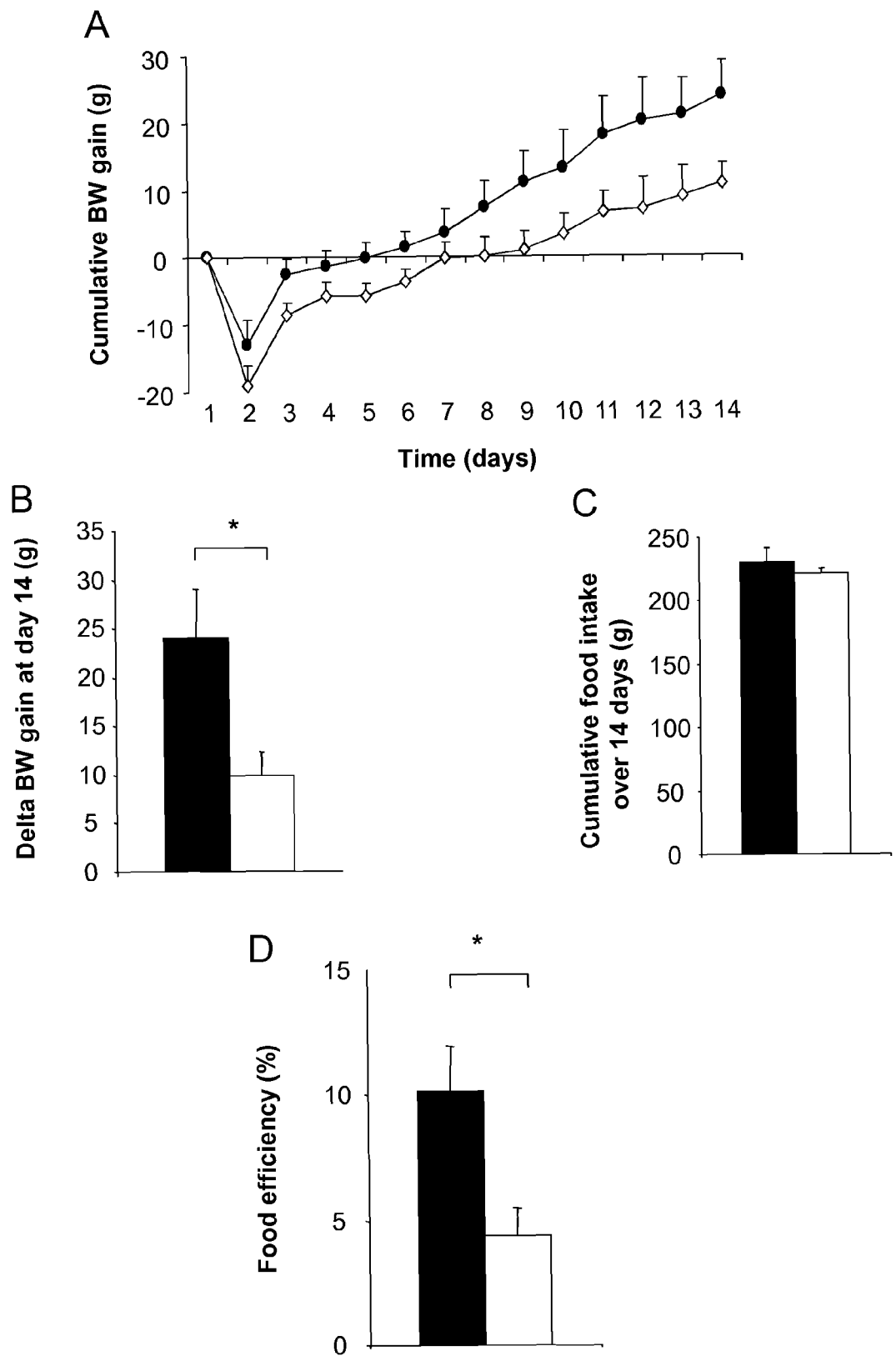
FIG. 1 shows the effect of central OT administration on body weight gain in a high-fat diet induced obesity rat model as described in Example 1. A: Cumulative body weight gain over the 14 day treatment period (week 5 to 7 of high fat diet, 45%) of (●) saline-infused controls and (◇) OT-infused rats (1.6 nmol/d). B: Delta body weight gain and C: cumulative food intake over the 14 day treatment period of saline-infused controls (black bars) and OT-infused rats (1.6 nmol/d) (white bars). D: Food efficiency (ratio of body weight gain to cumulative food intake over the 14-day experimental period).

The term "oxytocin derivative" as referred to herein, includes natural or synthetic, therapeutically or prophylactically active, peptide fragments, peptide analogues, and chemically modified derivatives or salts of active peptides presenting activity similar to or substantially retaining the activity of the parent molecule of oxytocin. For example, oxytocin derivatives include oxytocin or oxytocin peptide analogues which are chemically modified, for example, by amidation of the carboxyl terminus (—$NH_2$), the use of D amino acids in the peptidic sequence, incorporation of small non-peptidyl moieties, as well as the modification of the amino acids themselves (e.g. alkylation or esterification of side chain R-groups) (peptidomimetics). In particular, the term oxytocin derivative includes "oxytocin analogues" which means polypeptides substantially homologous to native human oxytocin, respectively, but which have an amino acid sequence different from that of native human oxytocin because of one or more deletions, insertions or substitutions. Substantially homologous means a variant amino acid sequence that is at least 80%, at least 85%, at least 90%, at least 95%, at least 96%, at least 97%, at least 98% or at least 99% identical to the native amino acid sequences, as disclosed above. The percent identity of two amino acid or two nucleic acid sequences can be determined by visual inspection and/or mathematical calculation, or more easily by comparing sequence information using known computer program used for sequence comparison such as Clustal package version 1.83. Oxytocin analogues may comprise a sequence having at least one conservatively substituted amino acid, meaning that a given amino acid residue is replaced by a residue having similar physiochemical characteristics. Oxytocin derivatives may include, but are not limited to those described in WO 2008/042452 or EP 1928484, the contents of which are herein incorporated by reference in their entirety, such as 4-threonine-1-hydroxydeaminooxytocin, 4-serine, 8-isoleucine-oxytocin, 9-deamidooxytocin, 7-D-proline-oxytocin and its deamino analog, (2,4-diisoleucine)-oxytocin, deamino oxytocin analog, a long acting oxytocin analog, 1-deamino-1-monocarba-E12-Tyr(OMe)]-OT(dCOMOT), carbetocin (SEQ ID NO: 2: Butyryl-Tyr(Me)-Ile-Gln-Asn-Cys-Pro-Leu-Gly-NH$_2$), 4-threonine, 7-glycine-oxytocin (TG-OT), (1-butanoic acid-2-(O-methyl-L-tyrosine)-1-carbaoxytocin, Ile-conopressin, atosiban, oxypressin, deamino-6-carba-oxytoxin (dC60), desmopressin, and 1-deamino-oxytocin in which the disulfide bridge between residues 1 and 6 is replaced by a thioether.

The term "oxytocin agonist" includes substances that are able to interact with the oxytocin receptor (OTR) and/or mimic the oxytocin biological activity, notably through its interaction with the OTR. For example, oxytocin agonists include those described in WO 2007/050353, WO 2005/023812, WO 2004/072083 and WO 03/016316, the contents of which are herein incorporated by reference in their entirety. Oxytocin agonists include peptides, peptidomimetics and small molecules. In particular, they include WAY-267,464 (4-(3,5-dihydroxybenzyl)-N-(2-methyl-4-[(1-methyl-4,10-dihydropyrazolo[3,4-b][1,5]benzodiazepin-5(1H)-yl)carbonyl]benzyl)piperazine-1-carboxamide), decomoton and 4,-(3,5-Dihydroxy-benzyl)-piperazine-1-carboxylic acid 2-methyl-4-(3-methyl-4,10-dihydro-3H-2,3,4,9-tetra-azabenzo[f]azulene-9-carbonyl)-benzylamide.

The term "peptidomimetic" is defined as a peptide analog containing non-peptidic structural elements, which peptide is capable of mimicking or agonizing the biological action(s) of a natural parent peptide.

Other useful forms of oxytocin derivatives, oxytocin analogs or oxytocin agonists in the context of the invention include other pharmaceutically acceptable active salts of said compounds, as well as active isomers, enantiomers, polymorphs, solvates, hydrates, and/or prodrugs of said compounds.

The term "pharmaceutically acceptable" refers to a carrier comprised of a material that is not biologically or otherwise undesirable.

The term "carrier" refers to any component present in a pharmaceutical formulation other than the active agent and thus includes diluents, binders, lubricants, disintegrants, fillers, coloring agents, wetting or emulsifying agents, pH buffering agents, preservatives and the like.

The term "obesity" includes a disease or disorder comprising having a high amount of body fat. Typically, obese humans have a body mass index (BMI) (an individual's body weight divided by the square of his or her height) of about 30 kg/m$^2$ or greater. Obesity is known to be accompanied by increased risks for several co-morbidities such as type 2 diabetes, hypertension, cardiovascular disease and arthritis.

The term "insulin resistance" refers to elevated blood glucose levels (fasting glucose is levels of 110-126 mg/dL; glucose levels of more than 140 mg/dL 2 hours after administration of 75 g of glucose).

The term "metabolic syndrome" refers to a cluster of syndromes including central obesity (excess fat in the abdomen measured by waist circumference, typically equal or higher than 80 cm in females and equal or higher than 90 cm in males) plus at least two other conditions selected from dyslipidaemia (in particular elevated serum triglycerides, typically equal or higher than 150 mg/dL and low levels of high density cholesterol (HDL), typically lower than 40 mg/dL in males and than 50 mg/dL in females), elevated blood pressure (BP), typically equal or higher than 130 mm Hg for systolic BP and equal or higher than 85 mm Hg for diastolic BP or insulin resistance.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions such as improvement or remediation of damage.

In particular, treatment of obesity comprises to normalize body weight or improve body overweight and in particular central fat deposit. Treatment of obesity also comprises a reduction of the risk of co-morbidities related to obesity mentioned above.

In particular, treatment of insulin resistance comprises to normalize or improve an impairment of normal biologic responses to either exogenous or endogenous insulin, typically through the control of blood glucose levels or insulin production. Treatment of insulin resistance comprises the prevention or slowing down of the progression of the syndrome towards type 2 diabetes.

In particular, treatment of metabolic syndrome comprises to normalize or improve at least one component of the syndrome, independently of weight loss. In a particular aspect, treatment of metabolic syndrome comprises the prevention of the development of type 2 diabetes.

The term "subject" as used herein refers to mammals. For examples, mammals contemplated by the present invention include human, primates, domesticated animals such as cattle, sheep, pigs, horses, laboratory rodents and the like.

The term "efficacy" of a treatment according to the invention can be measured based on changes in the course of disease in response to a use according to the invention. For example, the efficacy of a treatment according to the invention can be measured by a decrease in central obesity (e.g. wait circumference decrease, decrease in fat mass) or a decrease in insulin resistance by oral glucose tolerance test (OGTT), fasting glucose test (FPG) or euglycemic hyperinsulinemic clamp. For another example, the efficacy of the treatment of obesity encompasses a reduction of plasma triglycerides and the like.

Method of Preparation

Oxytocin, oxytocin derivatives, oxytocin agonists and oxytocin analogues are either commercially available (e.g. NeoMPS, Strasbourg, France) or can be readily prepared by the skilled person for example as described in U.S. Pat. No. 2,938,891 and U.S. Pat. No. 3,076,797 and tested for biological activity according to known methods. All peptidic oxytocin derivatives or analogues described and/or contemplated herein can be prepared by chemical synthesis using either automated or manual solid phase synthetic technologies or by using molecular recombinant techniques, techniques which as generally known in the art.

Compositions

The invention provides pharmaceutical or therapeutic agents as compositions and methods for treating a patient, preferably a mammalian patient, and most preferably a human patient who is suffering from a medical disorder, and in particular a disorder selected from obesity and insulin resistance.

In a particular embodiment, the invention provides pharmaceutical or therapeutic agents as compositions and methods for treating a patient, preferably a mammalian patient, and most preferably a human patient who is suffering from a medical disorder, wherein the disorder is metabolic syndrome.

In a particular embodiment, the invention provides pharmaceutical or therapeutic agents as compositions and methods for treating a patient, preferably a mammalian patient, and most preferably a human patient who is suffering from a medical disorder, wherein the is disorder is type 2 diabetes.

In a particular embodiment, the invention provides a pharmaceutical formulation according to the invention for use as a medicament.

Pharmaceutical compositions of the invention can contain at least one substance selected from oxytocin, an oxytocin derivative and an oxytocin agonist according to the invention in any form described herein. Compositions of this invention may further comprise one or more pharmaceutically acceptable additional ingredient(s) such as alum, stabilizers, antimicrobial agents, buffers, coloring agents, flavoring agents, adjuvants, and the like.

The compositions according to the invention, together with a conventionally employed adjuvant, carrier, diluent or excipient may be placed into the form of pharmaceutical compositions and may be employed as solids, such as tablets or filled capsules, or liquids such as solutions, suspensions, ointments, emulsions, elixirs, or capsules filled with the same, films or gels, all for oral use, or in the form of sterile injectable solutions for parenteral (including subcutaneous) use by injection or continuous infusion. If desired, sustained-release compositions, e.g. sustained-release gels, films, and transdermal patches can be readily prepared. The compositions may also be formulated as a dry product for reconstitution with water or other suitable vehicle before use.

Compositions of this invention as liquid formulations including, but not limited to, aqueous or oily suspensions, solutions, emulsions, syrups, and elixirs may be for use as drops, for use in an injection, as a spray or impregnated in a nasal tampon.

Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to a particular embodiment, compositions according to the invention are injectable or inhalable.

Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®. Further materials as well as formulation processing techniques and the like are set out in Part 5 of *Remington's Pharmaceutical Sciences*, $21^{st}$ Edition, 2005, University of the Sciences in Philadelphia, Lippincott Williams & Wilkins, which is incorporated herein by reference.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions of this invention may also be formulated for nasal delivery which may be in a form including, but not limited to powdered or liquid nasal spray, suspension, nose drops, a gel, film or ointment, through a tube or catheter, by syringe, by packtail, by pledget (small flat absorbent pad), by nasal tampon or by submucosal infusion. Nasal drug delivery can be carried out as described in EP 1928484 or WO 2008/042452, for example by using devices including, but not limited to, unit dose containers, pump sprays; droppers, squeeze bottles, airless and preservative-free sprays, nebulizers, metered dose inhalers, and pressurized metered dose inhalers. Nasal drug delivery devices are known in the art and several are commercially available. Aerosol sprays may be dispensed by using a pressurized pack or a nebulizer and a suitable propellant including, but not limited to, dichlorodifluoromethane, trichlorofluoromethane, dichlorotetrafluoroethane, hydrocarbons, compressed air, nitrogen or carbon dioxide. An aerosol system requires the propellant to be inert towards the pharmaceutical composition. In the case of a pressurized aerosol, the dosage unit may be controlled by providing a valve to deliver an accurately metered amount.

Powdered nasal sprays can be formulated in the form of microspheres delivered by a nasal insufflator device (device for blowing a gas, powder, or vapour into a cavity of the body) or pressurized aerosol canister.

The compounds of this invention can also be administered in sustained release forms or from sustained release drug delivery systems (WO 2004/078147). A description of representative sustained release materials can also be found in the incorporated materials in *Remington's Pharmaceutical Sciences.*

Mode of Administration

Compositions of this invention may be administered in any manner including intravenous injection, oral route, mucosal administration (delivery to the mucosal surfaces of the nose, nasal passageways, nasal cavity; to the mucosal surfaces of the oral cavity including the gingiva, the floor of the oral cavity, the cheeks, the lips, the tongue, the teeth; and to the mucosal surfaces of or around the eye including conjunctiva, lacrimal gland, nasolacrimal ducts, mucosa of the upper or lower eyelid and the eye), intranasal administration (e.g. by spray, drops, powder, gel, film, inhalant or other means), dermal or transdermal administration (e.g. delivery to the skin including the face, neck, scalp, body or combinations thereof) for example by intradermal or subcutaneous injection, or combinations thereof.

Combination

According to the invention, oxytocin, an oxytocin derivative and an oxytocin agonist and pharmaceutical formulations thereof can be administered alone or in combination with a co-agent useful in the treatment of obesity and/or insulin resistance, such as substances useful for treating, stabilizing, preventing, and/or delaying obesity and/or insulin resistance e.g. for example a co-agent selected from the classes of biguanides, glitazones, sulfonylureas, DPPIV inhibitors or GLP-1 agonists, as described in De Fronzo, 2010*, Am. J. Med,* 3(1), S38-48.

The invention encompasses the administration of a derivative selected from oxytocin, an oxytocin derivative and an oxytocin agonist and pharmaceutical formulations thereof to an individual prior to, simultaneously or sequentially with other therapeutic regimens or co-agents useful in the treatment of obesity and/or insulin resistance (e.g. multiple drug regimens), in a therapeutically effective amount. A derivative selected from oxytocin, an oxytocin derivative and an oxytocin agonist or the pharmaceutical formulations thereof that is administered simultaneously with said co-agents can be administered in the same or different composition(s) and by the same or different route(s) of administration.

According to one embodiment, is provided a pharmaceutical formulation comprising a derivative selected from oxytocin, an oxytocin derivative and an oxytocin agonist combined with at least one co-agent useful in the treatment of a disease or a disorder selected from obesity and insulin resistance, and at least one pharmaceutically acceptable carrier.

According to another embodiment, is provided a pharmaceutical formulation according to the invention wherein the derivative is oxytocin.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

In a particular embodiment, an effective amount of oxytocin, an oxytocin derivative, or an oxytocin agonist will depend on the form and composition being used for administration. Typically, the effective amount of oxytocin, an oxytocin derivative, or an oxytocin agonist administered transmucosally or transdermally is generally lower than dosages used when the agent is delivered by other routes (e.g. oral, intravenous, intramuscular or subcutaneous).

In a particular embodiment, dosages used for administration of oxytocin, an oxytocin derivative, or an oxytocin agonist include, but are not limited to, an effective amount within the dosage range of about 10 to about 1,500 μg, typically from about 20 to about 1,000 μg, such as from about 25 to about 750 μg.

In other particular embodiment, dosages used for administration of oxytocin, an oxytocin derivative, or an oxytocin agonist include dosages for nasal administration as described in EP 1928484 or WO 2008/042452.

Patients

In an embodiment, patients according to the invention are patients suffering from a disorder selected from obesity and insulin resistance.

In a further embodiment, patients according to the invention are patients suffering from obesity.

In another further embodiment, patients according to the invention are suffering from insulin resistance.

In another further embodiment, patients are suffering from metabolic syndrome.

In another further embodiment, patients are suffering from type 2 diabetes.

Use According to the Invention

In another embodiment of the invention is provided a use of a derivative selected from oxytocin, an oxytocin derivative and an oxytocin agonist for the preparation of a pharmaceutical composition for the repression or treatment of obesity and/or insulin resistance.

In a further embodiment, is provided a use of a derivative selected from oxytocin, an oxytocin derivative and an oxytocin agonist for the preparation of a pharmaceutical composition for the prevention or treatment of metabolic syndrome.

In a further embodiment, is provided a use of a derivative selected from oxytocin, an oxytocin derivative and an oxytocin agonist for the preparation of a pharmaceutical composition for the prevention or treatment of type-2 diabetes.

In another embodiment, the invention provides a method of prevention and/or treatment of a disease comprising the administration of a therapeutically effective amount of a derivative selected from oxytocin, an oxytocin derivative and an oxytocin agonist in a mammal in need thereof and wherein the disease is selected from obesity and/or insulin resistance.

In another embodiment, is provided a compound, a use or a method according to the invention, wherein the disorder is obesity.

In another embodiment, is provided a compound, a use or a method according to the invention, wherein the disorder is insulin resistance.

In another embodiment, is provided a compound, a use or a method according to the invention, wherein the derivative is oxytocin.

In another embodiment, is provided a compound, a use or a method according to the invention, wherein the derivative is an oxytocin analogue.

In another embodiment, is provided a compound, a use or a method according to the invention, wherein the oxytocin analogue is carbetocin.

In another embodiment, is provided a compound, a use or a method according to the invention, wherein the derivative is an oxytocin agonist.

Compounds and compositions according to the invention may be useful in the repression or treatment of obesity and/or insulin resistance. In a particular embodiment, compounds and compositions according to the invention may be useful in the repression or treatment of metabolic syndrome. In another particular, embodiment, compounds and compositions according to the invention may be useful in the repression or prevention or treatment of type-2 diabetes.

Examples illustrating the invention will be described hereinafter in a more detailed manner and by reference to the embodiments represented in the Figures.

EXAMPLES

The following abbreviations refer respectively to the definitions below: Acadm (medium chain acyl-CoA dehydrogenase), Acox1 (acyl-CoA oxidase 1) BAT (brown adipose tissue), Ci (Curie), d (day), h (hour), µg (microgram), mg (milligram), min (minute), mM (millimolar), nm (nanometer), ACACA (acetyl-coenzyme A carboxylase alpha), AEA (Anandamide), BW (Body weight), cDNA (complementary DNA), DGAT1 (diacylglycerol O-acyltransferase homolog 1), Ehhadh (enoyl-CoA hydratase/3-hydroxyacyl-CoA dehydrogenase), ELISA (Enzyme-linked immunosorbent assay), eWAT (epididymal white adipose tissue), FASN (fatty acid synthase), GIR (glucose infusion rate), GR (red gastrocnemius), GW (white gastrocnemius), HFD (high-fat diet), HSL (hormone-sensitive lipase), iWAT (inguinal WAT), Lpl (Lipoprotein lipase), M-MLV-RT (Moloney Murine Leukemia Virus Reverse Transcriptase), NEFA (Non-esterified fatty acids), OEA (Oleoylethanolamide), OT (oxytocin), PCR (Polymerase Chain Reaction), PEA (Palmitoylethanolamide), PNPLA2 (patatin-like phospholipase domain containing 2), QR (red quadriceps), QW (white quadriceps), RNA (Ribonucleic acid), RT (reverse transcriptase), S (soleus), SCD1 (stearoyl-Coenzyme A desaturase 1), TG (Triglycerides), TIB (tibialis), UCP3 (uncoupling protein 3), 2-AG (2-Arachidonoylglycerol).

Example 1

Positive Impact of Central or Peripheral OT Infusion on Body Weight Gain, Lipid Metabolism and Insulin Resistance The beneficial metabolic effects of OT administration were assayed in the following high-fat diet-induced obesity model in rats.
Animals and Diets Male Wistar (300-325 g) rats were purchased from Charles River (L'Arbresle, France) and housed in individual cages under conditions of controlled temperature (22° C.) and illumination (light on: 07:00-19:00 h). They were allowed free access to water and a 45% high fat diet (HFD) (metabolized energy, 4.56 kcal/g) (Ssniff® EF R/M acc. D12451 (I) mod., ssniff Spezialdiaten GmbH, Soest, Germany) for seven weeks. Body weight, food intake and water intake were recorded daily (08:30-09:30 h). All procedures were approved by the Ethic Committee of our University and were in accordance with the Swiss guidelines for animal experimentation.
Intracerebroventricular (i.c.v.) infusion To study the role of OT on metabolic homeostasis, the above male Wistar rats were rendered obese by 7 weeks of HFD 45% and were intracerebroventricularly (i.c.v.) infused with either OT (1.6 nmol/d) or saline during the last 2 weeks of the experiment.

After three weeks of HFD feeding, rats were submitted to surgical procedures. They were anesthetized with intramuscular injection of ketamine-xylasine (Ketalar®-Rompun®, Parke-Davis and Bayer, Leverkusen, Switzerland) at 40 and 9 mg/kg, respectively, and implanted with a cannula in the right lateral cerebral ventricle fixed on the skull with dental cement, as previously described (Rohner-Jeanrenaud et al., 1989, Endocrinology 124, 733-9). After one week of recovery, the drinking response to i.c.v. injection of Angiotensin II (5 ng/µl) (Novabiochem, Laüfelfingen, Switzerland) was measured to confirm the correct placement of the cannula. At the end of the fifth week of high fat diet feeding, osmotic minipumps (Alzet®, model 2001, Alza Corporation, Cupertino, Calif.) delivering oxytocin (NeoMPS®, Strasbourg, France) or its vehicle (NaCl 0.9%) were subcutaneously implanted and connected to the i.c.v. cannula via a polyethylene catheter, as previously described (Rohner-Jeanrenaud et al., 1989, above). OT was delivered at a dose of 1.6 nmol/day/rat or 16 nmol/day/rat during 14 days. A group of vehicle-infused rats was pair-fed to the amount of food consumed by OT-infused animals in order to assess the effects of OT independently from changes in food intake. The pair-feeding regimen consisted in giving one-third of the daily food amount in the morning and the remaining two-thirds just before onset of darkness. Rats were sacrificed using isoflurane anesthesia (Halocarbon Laboratories, River Edge, N.J.) and rapid decapitation between 09:00 and 13:00 h. Blood samples were collected into EDTA-coated tubes, centrifuged and plasma stored at −20° C. Tissues were rapidly removed, freeze-clamped, and stored at −80° C.
Subcutaneous (s.c.) Infusion Another group of the above male Wistar rats were rendered obese as described above and were subcutaneously infused with saline or OT (NeoMPS®, Strasbourg, France) (50 nmol/day/rat) during 14 days.
Glucose Tolerance Tests The impact of OT-induced changes in peripheral lipid metabolism on glucose tolerance and insulin sensitivity was determined by glucose tolerance tests (GTT). Glucose (75 mg/kg body weight) was intraperitoneally administered 4 h after food removal. Blood glucose levels were measured using a glucose meter (One Touch II; LifeScan) from tail blood samples at 0, 15, 30, 60, 90, and 120 min after glucose injection.
Euglycemic-Hyperinsulinemic Clamps Global and tissue-specific glucose utilization rates were measured by performing euglycemic-hyperinsulinemic clamps associated with the labeled 2-deoxyglucose technique as previously described (Vettor et al., 1994, *Diabetologia*, 37, 1202-1208). HFD-induced obese rats were overnight fasted and intraperitoneally anesthetized with Nembutal (75 mg/kg sodium pentobarbital; Abbott Laboratories, Chicago, Ill.). Total glucose utilization was measured during euglycemic-hyperinsulinemic clamps, as previously described (Vettor et al., 1994, above). At the end of the clamp, the in vivo insulin-stimulated glucose utilization index of individual tissues was determined by injecting a single bolus of labeled 2-deoxy-D-[1-3H]glucose (30 µCi; Amersham Biosciences UK, Little Chalfont, UK), as previously described (Vettor et al., 1994, above). Rats were killed by rapid decapitation, and tissues were rapidly removed, freeze-clamped, and stored at −80° C. Measurement of tissue concentration of 2-deoxy-d-[1-$^3$H] glucose-6-phosphate allowed calculation (Vettor et al., 1994, above) of the in vivo glucose utilization index of individual tissues and was expressed in ng/mg·min.

Plasma Measurements

To determine the effect of OT on peripheral metabolism, levels of plasma glucose, insulin, leptin, FFA, glycerol and TG were determined. Plasma glucose was measured by the glucose oxidase method (Glu, Roche Diagnostics GmbH, Rotkreuz, Switzerland). Plasma non-esterified fatty acid (NEFA) and triglyceride (TG) levels were determined using NEFA C and TG enzymatic PAP150 commercial kits from Wako Chemicals GmbH (Neuss, Germany) and Biomérieux (Marcy l'Etoile, France), respectively. Plasma OT levels were determined using an ELISA, as previously described (Pequeux et al., 2001, *Scand. J. Clin. Lab. Invest.*, 61, 407-415). Plasma glycerol levels were measured using the free Glycerol Reagent (Sigma). Central OT infusion promoted increased plasma OT levels, suggesting a potential direct effect on adipose tissue.

Tissue Processing and Real-Time RT-PCR

To delineate the mechanisms responsible for the effect on peripheral metabolism, the expression of enzymes involved in lipid metabolism was analyzed in adipose tissues (epididymal white and interscapular brown adipose tissues). Total RNAs were extracted from frozen tissue using a single-step extraction with Trizol reagent (Sigma-Aldrich, Buchs, Switzerland). RNA integrity was assessed by electrophoresis on a 1% agarose gel and concentration was determined by spectrophotometry. An amount of 2.5 μg of total RNAs was used for RT using random hexamers (Microsynth, Geneva, Switzerland), dNTPs (Promega Corporation, Madison, Wis., USA), RNasin as an RNase inhibitor (Promega Corporation) and the Moloney Murine Leukemia Virus Reverse Transcriptase (M-MLV-RT) enzyme kit (Invitrogen, Basel, Switzerland). For quantitative PCR (qPCR), amplification of genes was performed from 6.25 or 12.5 ng cDNA, using the SYBR® green PCR Master Mix (Applied Biosystems, Warrington, UK) and an ABI7500 machine (Applied Biosystems, Foster City, Calif.). All the primers were designed (FIG. 9, Table 1) with the PrimerExpress software (http://phym.unige.ch/) and used at a concentration of 200 to 300 nM for qPCR. Results were normalized to the expression levels of the housekeeping gene, ribosomal protein S29 (RPS29).

Role of OT Administration on Body Weight Gain Independently from Changes in Food Intake Chronic i.c.v. OT infusion lowered body weight gain and resulted in a more than fifty percent decrease in cumulative body weight gain compared with the effect of saline (FIGS. 1A & 1B; P<0.05), without any effect on food intake (FIG. 1C). This resulted in a marked decrease in food efficiency in OT-treated rats compared to saline-infused controls, an index calculated as the ratio of body weight gain to cumulative food intake over the 14-day experimental period (FIG. 1D; P<0.05).

Role of OT Administration on Lipid Metabolism

All measured peripheral metabolism parameters (i.e. plasma glucose, insulin, leptin and FFA levels) were unchanged by central OT administration, compared to saline infusion, except plasma TG concentrations which were decreased, as shown in Table 2 below.

TABLE 2

|  | Saline-infused (control rats) | Oxytocin-infused (treated rats) |
| --- | --- | --- |
| Oxytocin (pg/ml) | 7.5 ± 2.0 | 21.8 ± 5.8 * |
| Glucose (mg/dl) | 159.1 ± 5.7 | 159.5 ± 4.1 |
| Insulin (ng/ml) | 2.5 ± 0.7 | 1.7 ± 0.3 |
| Leptin (ng/ml) | 13.9 ± 3.7 | 11.3 ± 2.2 |

TABLE 2-continued

|  | Saline-infused (control rats) | Oxytocin-infused (treated rats) |
| --- | --- | --- |
| FFA (mmol/l) | 0.82 ± 0.06 | 0.70 ± 0.06 |
| TG (mmol/l) | 1.11 ± 0.09 | 0.80 ± 0.05 * |
| OEA (pmol/ml) | 145 ± 13 | 178 ± 15 |
| PEA (nmol/ml) | 1.34 ± 0.16 | 1.63 ± 0.15 |
| AEA (pmol/ml) | 18 ± 2.9 | 19 ± 2.3 |
| 2-AG (pmol/ml) | 78 ± 13 | 53 ± 4.9 |

Values are mean ± SEM of 6-7 animals per group.
* P < 0.05 versus controls.
P = NS for all other comparisons.
Oleoylethanolamide (OEA),
Palmitoylethanolamide (PEA),
Anandamide (AEA) and
2-Arachidonoylglycerol (2-AG)

Figure 7:
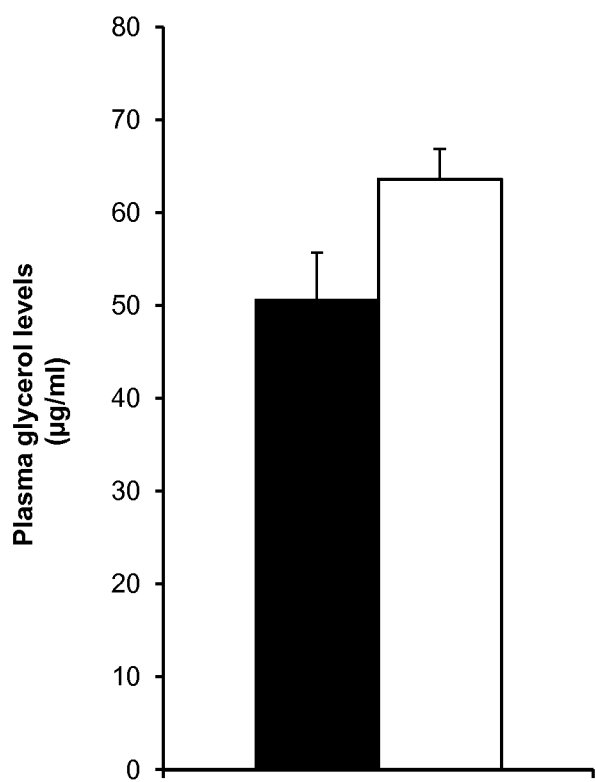
FIG. 7 shows the effect of (A) central and (B) peripheral OT administration on plasma glycerol levels in a rat model of high-fat diet-induced obesity as described in Examples 1 & 5. A: plasma glycerol levels of saline-infused controls (black bar) and OT-infused rats (1.6 nmol/day) (white bar). B: plasma glycerol levels of saline-infused controls (black bar), OT-infused rats (50 nmol/day) (white bar) and PF controls (grey bar). Values are mean±SEM of 6 to 8 animals per group.
Figure 7:
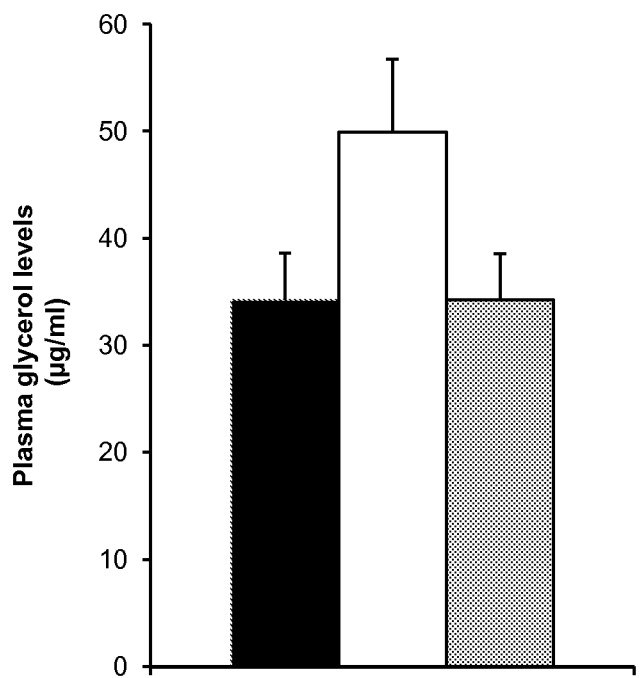

Further, both central (FIG. 7A) and peripheral (FIG. 7B) OT administration increased plasma glycerol levels, supporting that chronic OT administration increases lipolysis.

Figure 2:
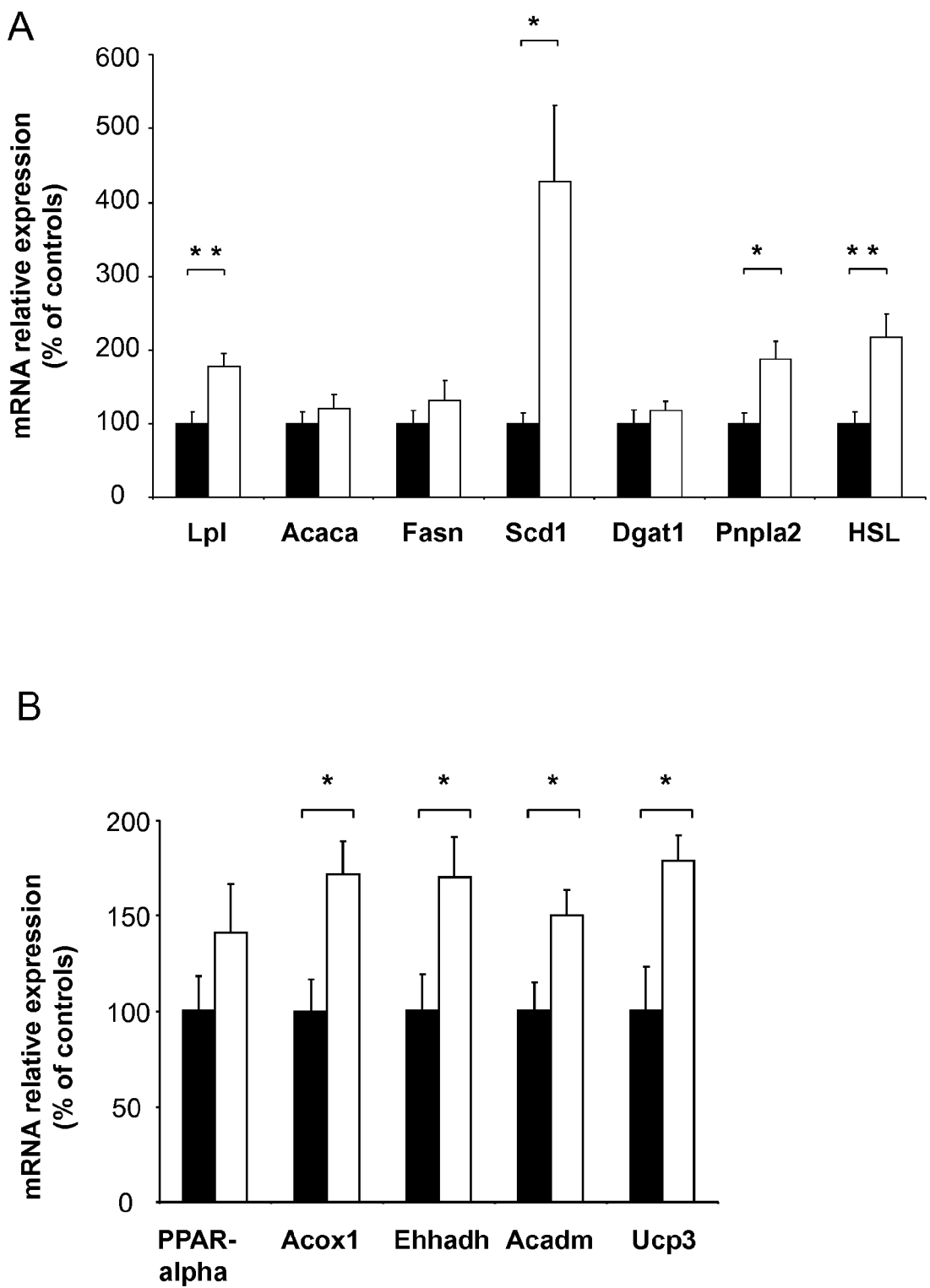
FIG. 2 shows the effect of central OT administration on lipid metabolism in a high-fat diet-induced obesity rat model as described in Example 1. A: mRNA expression of enzymes involved in triglyceride uptake, lipogenesis and lipolysis in epididymal white adipose tissue (eWAT) of saline-infused controls (black bars) and OT-infused rats (1.6 nmol/d) (white bars). B: mRNA expression of PPAR-alpha and of enzymes involved in fatty acid β-oxidation in epididymal white adipose tissue (eWAT) of saline-infused controls (black bars) and OT-infused rats (1.6 nmol/d) (white bars).

In epididymal white adipose tissue (eWAT), considered as an intra-abdominal fat depot, central OT infusion promoted an increase in the mRNA expression of Lpl, an enzyme responsible for the uptake of circulating TG (FIG. 2A; P<0.01). Central OT infusion did not modify the mRNA expression of enzymes involved in lipogenesis and TG storage [e.g., acetyl-coenzyme A carboxylase alpha (Acaca, also known as ACC-alpha), fatty acid synthase (Fasn) and diacylglycerol O-acyltransferase homolog 1 (Dgat1)] (FIG. 2A), whereas it increased that of two enzymes involved in lipolysis, namely patatin-like phospholipase domain containing 2 (Pnpla2) (FIG. 2A; P<0.05) and hormone-sensitive lipase (HSL) (FIG. 2A; P<0.01). The stimulatory effect of OT on HSL was also detected at the protein level.

As an enhanced intracellular availability of FFA in adipocytes would be expected as a result of such an increased TG uptake and lipolysis in OT-infused rats (1.6 nmol/d) compared to controls, the observation of actually unaltered plasma FFA levels in OT-infused rats (Table 2) suggests an endogenous utilization of these substrates induced by OT administration.

The measurement of mRNA expression of enzymes involved in fatty acid β-oxidation by real time RT-PCR as described above showed that OT infusion increased the eWAT expression of acyl-CoA oxidase 1 (Acox1, FIG. 2B, P<0.05), enoyl-CoA hydratase/3-hydroxyacyl-CoA dehydrogenase (Ehhadh, FIG. 2B, P<0.05) and medium chain acyl-CoA dehydrogenase (Acadm, also known as MCAD, FIG. 2B, P<0.05) and also enhanced the expression of the fatty acid sensing protein, uncoupling protein 3 (Ucp3, FIG. 2B, P<0.05). For the sake of comparison, the mRNA expression of most of the above genes was also analyzed in interscapular brown adipose tissue (BAT) and it was observed that OT infusion significantly increased the expression of the main enzymes involved in fatty acid β-oxidation as well as that of PPAR-alpha in this tissue. In contrast, central OT infusion did not modify the expression of genes involved in fatty acid β-oxidation in the liver and skeletal muscle. Further, central OT infusion promoted a marked increase in the mRNA expression of stearoyl-Coenzyme A desaturase 1 (Scd1) that converts the unsaturated fatty acids palmitic acid (16:0) and stearic acid (18:0) to the monounsaturated fatty acids palmitoleic acid (16:1) and oleic acid (18:1), respectively (FIG. 2A; P<0.05). It is known that those resulting fatty acids can either be incorporated into the membrane as phospholipids or stored as TG. As no change in the mRNA expression of enzymes involved in TG storage was observed in eWAT from OT-infused animals (FIG. 2A), an OT-induced increase in synthesis and incorporation as phospholipids (PL) into the membrane of palmitoleic or oleic acids could have occurred. Oleoylethanolamide (OEA), a member of the endocannabinoid family, results from the cleavage of N-oleoyl-phosphatidylethanolamine (NOPE) by N-acyl-phosphatidylethanolamine phospholipase D (NAPE-PLD), NOPE resulting from the transfer of oleic acid from the sn-1 position of phosphatidylcholine (PC) to the free amine of phosphatidylethanolamine (PE). It is observed that chronic i.c.v. OT infusion increased eWAT OEA content compared with the effect of saline, while not modifying the eWAT content of other endocannabinoids, such as the OEA saturated analog, palmitoylethanolamide (PEA) derived from palmitoleic acid, anandamide (AEA) or 2-arachidonoylglycerol (2-AG), nor did it alter plasma levels of OEA and of other endocannabinoids (Table 2).

To verify the hypothesis that central OT infusion modulates peripheral lipid metabolism by promoting OEA synthesis in adipose tissue, HFD-induced obese rats were i.c.v. infused for 14 days with a ten-fold higher dose of OT (16 nmol/d). At this dose, central OT infusion decreased cumulative food intake compared with i.c.v. saline-infused controls Therefore, to determine the metabolic effects elicited by OT independently from changes in food intake, a second saline-infused control group was pair-fed (PF) to the amount of food consumed by OT-treated rats. Body weight gain of i.c.v. OT-infused rats was significantly lower than that of the saline-infused control group, an effect that was independent from changes in food intake, as it was not observed in the PF control group. The stimulatory effect of this dose of OT on Scd1 mRNA expression and OEA content was more marked than that of the lower dose (5.6 and 2 folds versus 4.2 and 1.3 folds, respectively), being unrelated to changes in food intake, further supporting that central OT action on lipid metabolism in adipose tissue involves OT-promoted OEA synthesis.

In agreement with the results obtained with the ten-fold lower dose, infusion of 16 nmol/d of OT did not modify eWAT PPAR-alpha mRNA, but resulted in food intake-independent increases in the expression of PPAR-alpha target genes (e.g. Acadm, Acox1, Ehhadh, Ucp3). OT infusion significantly increased the mRNA expression of PPAR-alpha and its target genes in BAT. A potential effect of OT on BAT activity, including increased thermogenesis, cannot therefore be excluded.

Role of OT administration on high fat diet-induced insulin resistance

Figure 3:
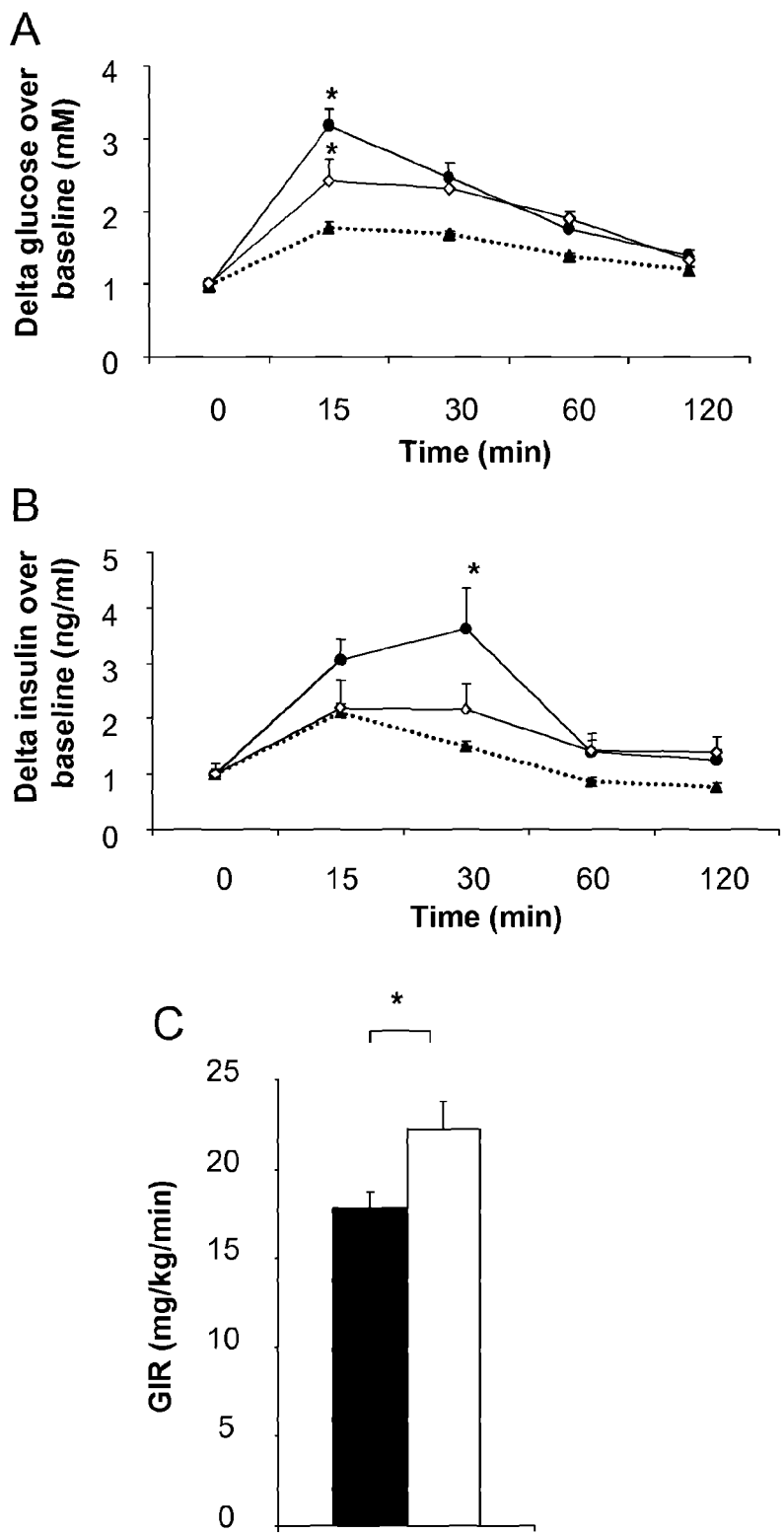
FIG. 3 shows the effect of central OT administration against high fat diet-induced insulin resistance as described in Example 1. A: delta glucose and B: delta insulin levels measured during intraperitoneal GTT (1.5 g/kg) before treatment (A) (3 weeks of high fat diet, 45%; n=16 rats), at the end of the treatment (7 week of high fat diet, 45%; n=6 is for each treatment) for (●) saline-infused controls and (◇) OT-infused rats (1.6 nmol/d). C: Glucose infusion rate (GIR) during euglycemic-hyperinsulinemic clamps in HFD-induced obese saline-infused controls (black bar) and OT-infused rats (white bar) (14-day intracerebroventricular (i.c.v.) OT infusion (1.6 nmol/d)). D & E: insulin-stimulated glucose utilization index measured during euglycemic-hyperinsulinemic clamps in different types of muscles (D): red quadriceps (QR), white quadriceps (QW), red gastrocnemius (GR), white gastrocnemius (GW), soleus (S), tibialis (Tib) (14-day i.c.v. OT infusion (1.6 nmol/d)) and in different types of adipose tissue depots (E): inguinal WAT (iWAT) and epididymal WAT (eWAT) of HFD-induced obese saline-infused controls (black bars) and OT-infused rats (white bars).
Figure 3:
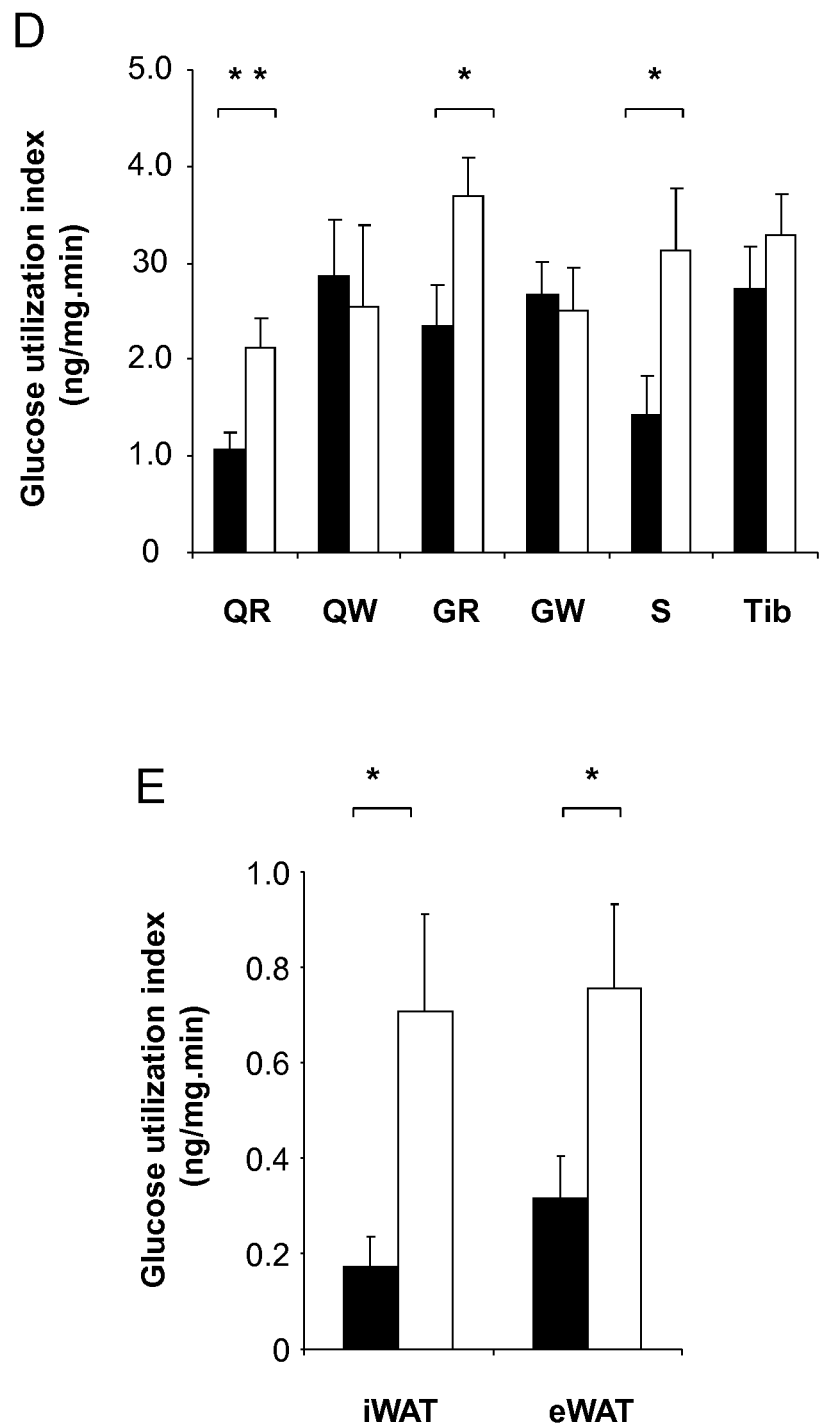

Two glucose tolerance tests (GTT) were performed, a first one after 3 weeks of HFD (i.e. before the respective saline and OT treatments) and a second one at the end of the 2 week saline or OT infusion (i.e. after 7 weeks of HFD). After 7 weeks of HFD, both saline- and OT-infused rats exhibited an impairment of glucose tolerance compared to the GTT performed after 3 weeks of HFD feeding (FIG. 3A; $P<0.05$). Such impairment was accompanied by insulin oversecretion in the saline-infused group (FIG. 3B; $P<0.05$), implying the occurrence of decreased insulin sensitivity while this was not observed in OT-infused animals, suggesting a protecting role for OT against HFD-induced glucose intolerance and insulin resistance. Euglycemic-hyperinsulinemic clamps experiments confirmed that OT infusion promoted significant increases in the glucose infusion rate (GIR) (FIG. 3C; $P<0.05$) and the glucose utilization index in red skeletal muscles, such as the red quadriceps (FIG. 3D; $P<0.01$), the red gastrocnemius (FIG. 3D; $P<0.05$), and the soleus (FIG. 3D; $P<0.05$) compared to saline group. A significant increase in glucose uptake in inguinal (FIG. 3E; $P<0.05$) and epididymal WAT (FIG. 3E; $P<0.05$), was also observed in rats centrally infused with OT.

Altogether, those results support that chronic central OT infusion decreases body weight gain in high fat diet (HFD)-induced obese rats, independently from changes in food intake, improves HFD-induced insulin resistance (improved glucose tolerance, together with a significant decrease in insulin secretion during GTT, i.e. improved insulin sensitivity, increased GIR and glucose utilization index in red skeletal muscles, iWAT and eWAT), decreases plasma triglyceride levels and increases the epididymal white adipose tissue (eWAT) expression of Lpl, an enzyme responsible for TG uptake, as well as that of enzymes involved in lipolysis and fatty acid β oxidation. This effect selectively targets white adipose tissue as chronic central OT infusion had no effect on lipid metabolism in skeletal muscle or in the liver. Further, the OT-elicited increase in eWAT OEA content and upregulation of genes (e.g. Acadm, Acox1, Ehhadh, Ucp3) coding for enzymes involved in fatty acid β-oxidation which are PPAR-alpha target genes (Jeong et al., 2009, *Exp. Mol. Med.*, 41, 397-405) supports an effect of OT in enhancing PPAR-alpha activity.

Example 2

Direct Effect of OT on Lipid Metabolism in Adipocytes In Vitro

The in vitro effect of OT on lipid metabolism in differentiated 3T3-L1 adipocytes was assayed as follows. Murine 3T3-L1 fibroblasts were differentiated towards a preadipocyte phenotype as previously described (Olson et al., 1997, *Mol. Cell. Biol.*, 2425-2435). In brief, cells were cultured in Dulbecco's modified eagle medium (DMEM) with 4.5 g/l glucose supplemented with 10% heat-inactivated depleted calf serum (DCS) at 37° C./8% CO2. Cells were induced to differentiate, two days post confluence, by sequential incubations with: DMEM 4.5 g/l glucose, 10% fetal bovine serum (FCS) containing 1 μg/ml insulin, 0.25 μM dexamethasone and 0.5 mM isobutylmethylxanthane (IBMX) for 4 days; DMEM 4.5 g/l glucose, 10% FCS containing insulin alone for an additional 4 days; DMEM 4.5 g/l glucose, 10% FCS for 3-4 days. Differentiation was considered achieved when more than 90% of cells display an accumulation of large lipid droplets in their cytoplasm.

Figure 4:
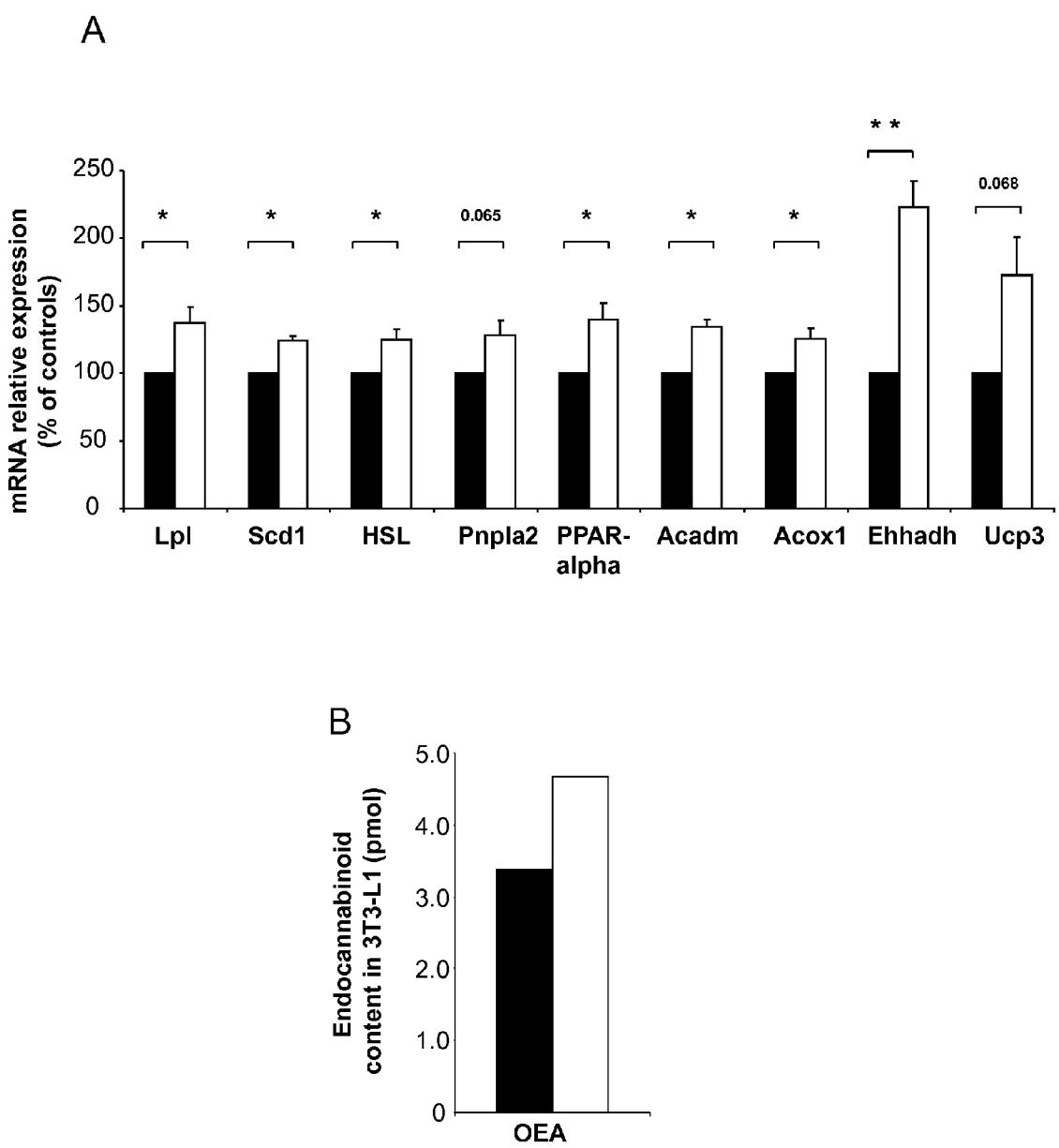
FIG. 4 shows the direct effect of OT on lipid metabolism in adipocytes in vitro as described in Example 2. A: mRNA expression of lipid metabolism-related enzymes in differentiated 3T3-L1 adipocytes after 24 h incubation with saline (black bars) or 5 µM OT (white bars) (three independent experiments performed on different series of cultured 3T3 µl adipocytes) B: OEA content in differentiated 3T3 µl adipocytes after 24 h incubation with saline (black bar) or 5 µM OT (white bar) (two independent experiments performed on different series of cultured 3T3 L1 adipocytes).

OT increased the mRNA expression of all the lipid metabolism-related genes that were affected by central OT infusion. This comprised a stimulatory effect of OT on PPAR-alpha (FIG. 4A). Furthermore and although the effect of OT on Scd1 mRNA expression was less marked than that obtained in centrally infused rats, exposure of 3T3-L1 adipocytes to OT resulted in an increased OEA content (FIG. 4B). To further support that OEA might be a mediator of OT-induced effects on lipid metabolism in adipose tissue, 3T3-L1 adipocytes were incubated in the presence of OEA and OEA showed to induce the mRNA expression of PPAR-alpha and of most of the PPAR-alpha related genes (Acadm, Acox1, Ehhadh, Ucp3).

Example 3

Positive Impact of Peripheral OT Administration on Body Weight Gain and Lipid Metabolism The beneficial metabolic effects of OT administration were assayed in the same high-fat diet induced obesity model in rats as in Example 1 and in PPAR-alpha knockout mice (Lee et al., 1995, *Mol. Cell. Biol.*, 15(6):3012-22). HFD-induced obese animals, saline or OT groups (see conditions under Example 1) were subcutaneously infused via minipumps (Alzet®, as above). OT was delivered at a dose of 50 nmol/day/rat during 14 days.

Body Composition Parameters

An EchoMRI-700 quantitative nuclear magnetic resonance (QMR) analyzer (Echo Medical Systems, Houston, Tex.) was used to measure total fat mass and lean body mass in rats at the beginning and the end of the treatment.

Figure 5:
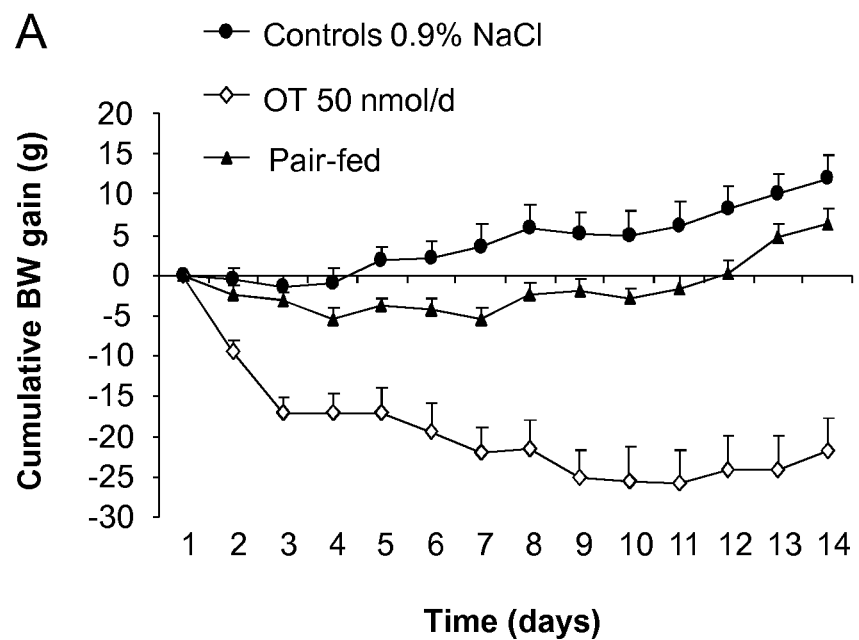
FIG. 5 shows the effect of peripheral OT administration in a high-fat diet-induced obesity rat model as described in Example 3. A: Cumulative body weight gain over the 14 day treatment period (week 5 to 7 of high fat diet, 45%) of (●) saline-infused controls, (◇) OT-infused rats (50 nmol/d) and (▲) pair-fed (PF) controls. B: Cumulative food intake over the 14 day experiment period of saline-infused controls (black bar), OT-infused rats (50 nmol/d, white bar) and PF controls (grey bar). C: Body composition parameters (fat and lean body masses) over a 10 day (D10) treatment period of saline-infused controls (black bar), OT-infused rats (50 nmol/d, white bar) and PF controls (grey bar). D: Delta body composition parameters between the beginning (D0) and the end (D10) of a 10 day treatment period. E: Ratio of different fat pad weight (inguinal WAT, iWAT; epididymal WAT, eWAT) over body weight of saline-infused controls (black bar), OT-infused rats (50 nmol/d, white bar) and PF is controls (grey bar). Values are mean±SEM of 7 to 8 animals per group. *$P<0.05$ compared to controls. F: Photographs of freshly dissected epididymal (eWAT) and mesenteric (mWAT) fat pads of saline-infused controls, OT-infused rats (50 nmol/d) and PF controls.
Figure 5:
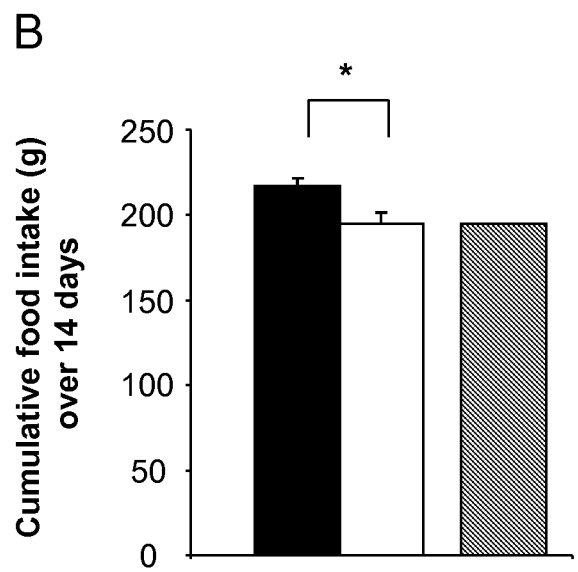
Figure 5:
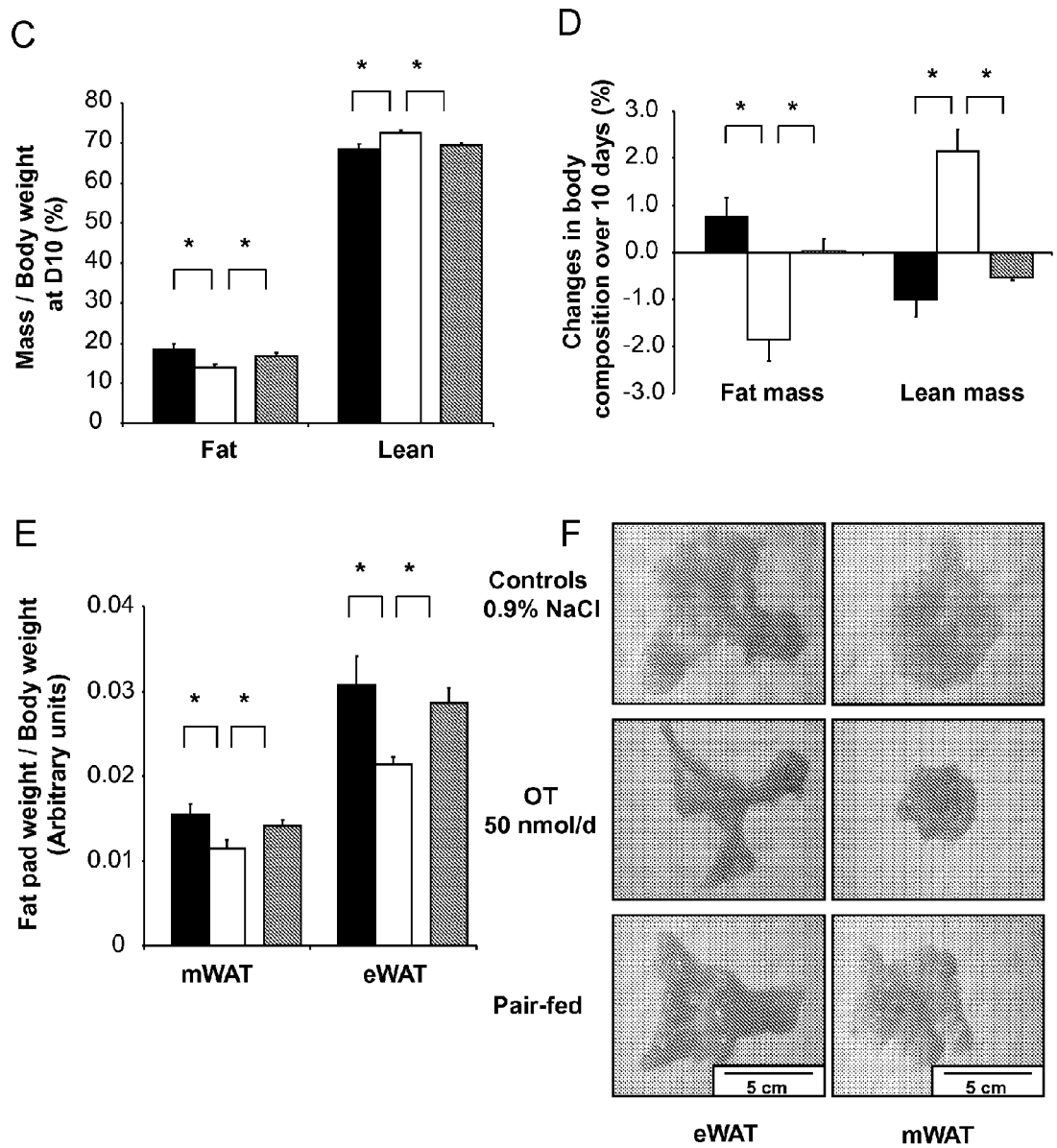

At this dose, OT administration decreased food intake (FIG. 5B; $P<0.05$) and body weight gain (FIG. 5A; $P<0.05$). Body weight loss of OT-treated rats was nevertheless unrelated to an anorexigenic effect of the hormone, as it was not observed in the PF group (FIG. 5A). The body composition analyzed by a QMR analyzer showed that the peripheral administration of OT promoted a significant decrease in fat mass, while inducing an increase in the percent lean body mass, independently from changes in food intake (FIGS. 5C and D; $P<0.05$) after 10 days of treatment. Such a food intake-independent decrease in fat mass was also confirmed by examining and weighing different adipose tissue depots (FIGS. 5E and F).

PPAR-Alpha Knockout and Wild-Type Mice

OT was peripherally administered with 50 nmol/day over 3 days in PPAR-alpha knockout (KO) mice and their wild-type littermates. While peripheral OT infusion induced a significant decrease in body weight gain of wild-type animals, it did not modify this parameter in PPAR-alpha KO mice. Consistently, OT peripheral infusion promoted an increase in the mRNA expression of PPAR-alpha target genes (Acadm, Acox1, Ehhadh, Ucp3) in wild-type mice, while it had no effect in PPAR-alpha knockouts.

Statistical Analyses

For examples 1-3, results are expressed as means±SEM. The Levene test was used to check for the equality of variance among groups (SPSS Inc., Chicago, Ill.). To assess the effects of treatment, groups' comparison was performed using parametric (Student's t test) and non-parametric (Mann-Whitney test) tests when normality and equal variance tests failed. Statistical significance was established at $*P<0.05$, $**P<0.01$.

These results support that OT-induced effects on adipose tissue lipid metabolism are exerted by direct activation of the PPAR-α pathway, stimulating the synthesis of the endocannabinoid, oleoylethanolamide (OEA) in adipose tissue and thereby stimulating lipolysis and local fatty acid oxidation.

All the observed metabolic effects support the benefit of OT administration and/or the activation of the OT receptor pathway by OT-like molecules (e.g. OT derivatives, OTR agonists or OT analogues) for the repression or treatment of obesity or insulin resistance. In particular, those multiple component effects support the benefit of OT administration and/or the activation of the OT receptor pathway by OT-like molecules for the treatment of a multi-component syndrome such as metabolic syndrome and in the prevention, repression, delay or treatment of disorders due to increased peripheral insulin resistance such as type 2 diabetes.

Example 4

Positive Impact of Peripheral OT Administration on High Fat Diet-Induced Insulin Resistance The beneficial effects of OT administration were assessed in the same rat model of high-fat diet induced obesity as in Example 1. HFD-induced obese animals were subcutaneously infused via minipumps (Alzet®, as above) with saline or OT (NeoMPS®, Strasbourg, France) (50 nmol/day/rat) during 14 days.

Homeostasis Model Assessment of Insulin Resistance

Insulinemia and glycemia were measured after an overnight fast before the euglycemic hyperinsulinemic clamps) and were used to calculate the "homeostasis model assessment of insulin resistance" (HOMA-IR). HOMA-IR was calculated as follows: (fasting serum insulin in mU/l)×(fasting blood glucose in mM)/22.5.

The effect of peripheral OT administration on high fat diet-induced insulin resistance was determined as described in Example 1.

Figure 6:
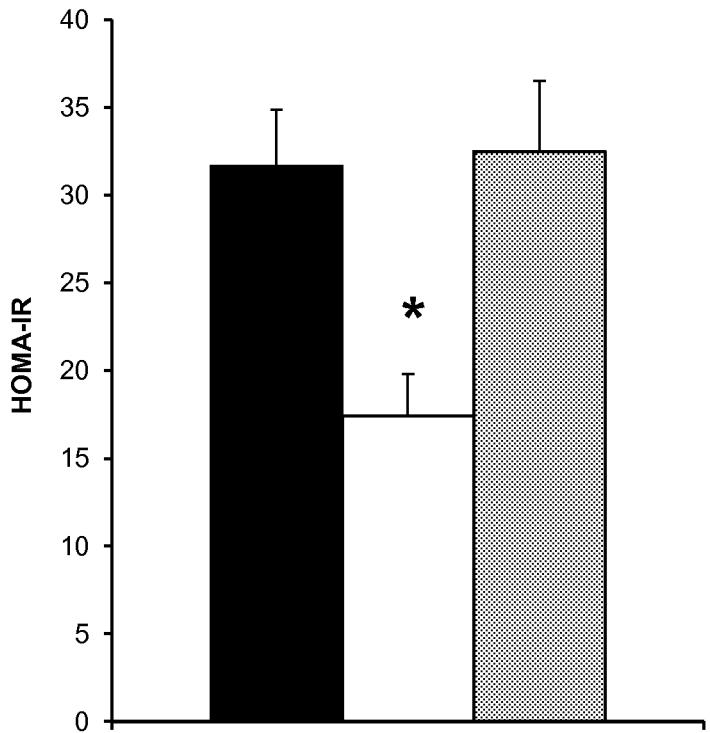
FIG. 6 shows the effect of peripheral OT administration on high fat diet (HFD)-induced insulin resistance as described in Example 4. A: Homeostasis model assessment of insulin resistance (HOMA-IR) of saline-infused controls (black bar), OT-infused rats (50 nmol/day) (white bar) and pair-fed (PF) controls (grey bar). B: Glucose infusion rate (GIR) during euglycemic-hyperinsulinemic clamps in HFD-induced obese saline-infused controls (black bar), OT-infused rats (50 nmol/day) (white bar) and PF controls (grey bar). Values are mean±SEM of 7 to 9 animals per group. *$P<0.05$ compared to controls.
Figure 6:
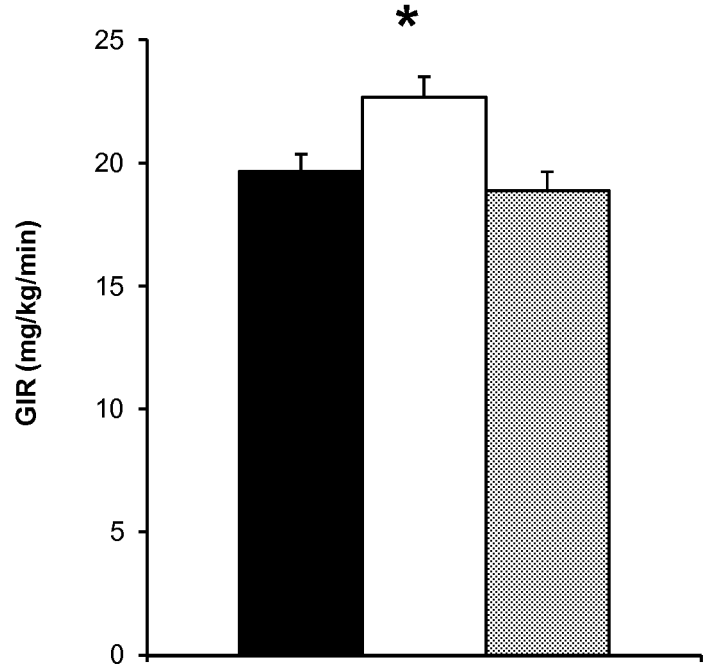

After 7 weeks of HFD, OT-infused rats exhibited a lower HOMA-IR as compared to saline-infused controls (FIG. 6A). This effect was unrelated to an anorexigenic effect of the hormone, as it was not observed in the PF group (FIG. 6A). Euglycemic-hyperinsulinemic clamps confirmed that OT infusion promoted an increased insulin sensitivity as it significantly increased the glucose infusion rate (GIR) (FIG. 6B) suggesting. Altogether, these results show that chronic peripheral OT infusion improves HFD-induced insulin resistance (decreased HOMA-IR and increased GIR).

Example 5

Positive Impact of Peripheral Carbetocin Administration on Body Weight Gain and Lipid Metabolism The beneficial metabolic effects of administration of an oxytocin derivative according to the invention (Carbetocin) were assessed in the same rat model of high-fat diet induced obesity as in Example 1. HFD-induced obese animals were subcutaneously infused via minipumps (Alzet®, as above) with saline or carbetocin (Bachem) (5 nmol/day/rat or 50 nmol/day/rat) during 14 days.

Body composition parameters were measured by quantitative nuclear magnetic resonance as described in Example 3 at the beginning and 10 days of treatment.

Figure 8:
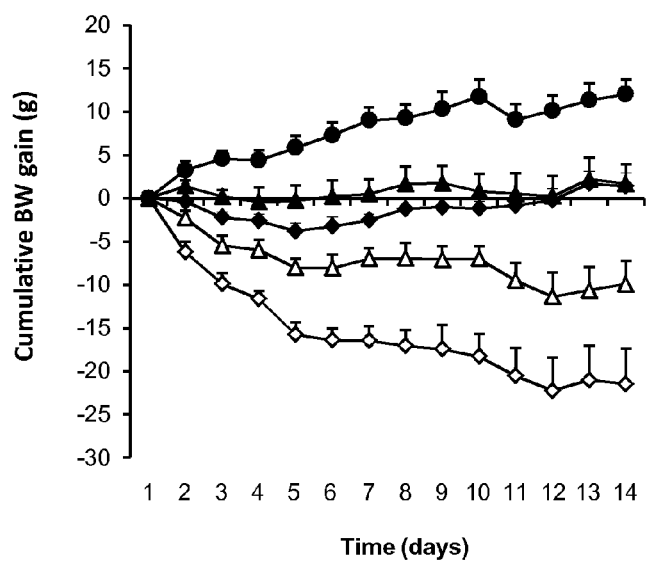
FIG. 8 shows the effect of peripheral carbetocin administration in a rat model of high-fat diet-induced obesity as described in Example 6. A: Cumulative body weight gain over the 14 day treatment period (week 5 to 7 of high fat diet, 45%) of (●) saline-infused controls, (Δ) carbetocin-infused rats (5 nmol/d) and associated (▲) pair-fed (PF) controls, (◇) carbetocin-infused rats (50 nmol/d) and associated (◆) PF controls. B: Cumulative food intake over the 14 day experiment period of saline-infused controls (black bar), carbetocin-infused rats (5 nmol/d, white bar) and associated PF controls (grey bar), carbetocin-infused rats (50 nmol/d, hatched white bar) and associated PF controls (hatched grey bar). C: Percent changes in body fat over a 10 day treatment period in saline-infused controls (black bar), carbetocin-infused rats (5 nmol/d, white bar) and associated PF controls (grey bar), carbetocin-infused rats (50 nmol/d, hatched white bar) and associated PF controls (hatched grey bar). Values are mean±SEM of 7 to 8 animals per group. *$P<0.05$ compared to controls.
Figure 8:
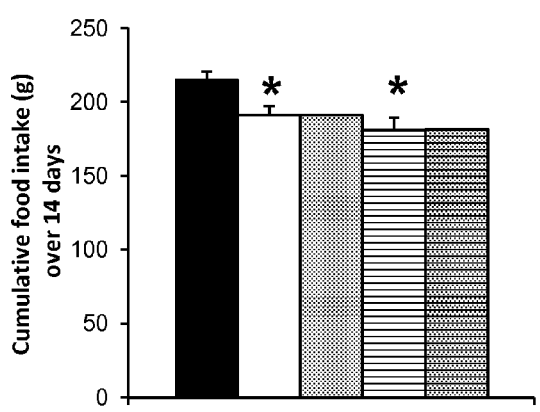
Figure 8:
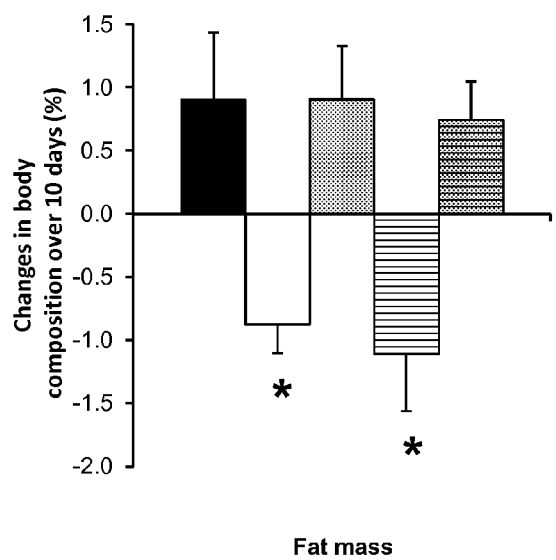

At both 5 nmol/day and 50 nmol/day, carbetocin administration decreased food intake (FIG. 8B; $P<0.05$) and body weight gain (FIG. 8A; $P<0.05$). Body weight loss of carbetocin-treated rats was nevertheless unrelated to an anorexigenic effect of the peptide, as it was not observed in the two PF groups (FIG. 8A). The body composition determined with a QMR analyzer showed that the peripheral administration of carbetocin promoted a significant decrease in fat mass independently from changes in food intake (FIG. 8C; $P<0.05$) after 10 days of treatment.

Overall, all the observed effects support the benefit of OT administration and/or the activation of the OT receptor pathway by OT-like molecules (e.g. OT derivatives, OTR agonists or OT analogues) for the repression or treatment of obesity or insulin resistance.

The invention claimed is:

1. A method of treating or reducing insulin resistance in a subject, said method comprising administering to a subject having insulin resistance a therapeutically effective amount of an oxytocin agonist selected from oxytocin, an oxytocin derivative which retains the biological activity of native oxytocin and an oxytocin agonist, or a pharmaceutical formulation thereof, wherein the oxytocin, oxytocin derivative or oxytocin agonist is to be administered peripherally.

2. The method according to claim 1, wherein the oxytocin agonist is oxytocin.

3. The method according to claim 1, wherein the oxytocin agonist is carbetocin.

4. The method according to claim 1, wherein the oxytocin agonist is an oxytocin analogue.

5. The method according to claim 1, wherein the subject is obese.

6. The method according to claim 1, wherein the subject is suffering from metabolic syndrome.

7. The method according to claim 1, wherein the subject is suffering from type-2 diabetes.

8. The method according to claim 1, wherein the pharmaceutical formulation comprises an oxytocin agonist selected from oxytocin, an oxytocin derivative which retains the biological activity of native oxytocin, and an oxytocin agonist, combined with at least one co-agent useful in the treatment of a disease or a disorder selected from obesity and insulin resistance, and at least one pharmaceutically acceptable carrier.

9. The method according to claim 1, wherein the oxytocin, oxytocin derivative or oxytocin agonist is administered in combination with at least one co-agent useful in the treatment of a disease or a disorder selected from obesity and insulin resistance.

10. The method according to claim 9, wherein the co-agent is a biguanide, glitazone, sulfonylurea, DPPIV inhibitor or GLP-1 agonist.

11. The method according to claim 1, wherein the oxytocin derivative is selected from 4-threonine-1-hydroxydeaminooxytocin, 4-serine, 8-isoleucine-oxytocin, 9-deamidooxytocin, 7-D-proline-oxytocin, (2,4-diisoleucine)-oxytocin, 1-deamino-1-monocarba-E12-Tyr(OMe)]-OT(dCOMOT), carbetocin (SEQ ID NO: 2: Butyryl-Tyr(Me)-Ile-Gln-Asn-Cys-Pro-Leu-Gly-NH$_2$), 4-threonine, 7-glycine-oxytocin (TG-OT), (1-butanoic acid-2-(O-methyl-L-tyrosine)-1-carbaoxytocin, Ile-conopressin, atosiban, oxypressin, deamino- 6-carba-oxytoxin (dC60), desmopressin and 1-deamino-oxytocin in which the disulfide bridge between residues 1 and 6 is replaced by a thioether.

\* \* \* \* \*

SEQUENCE LISTING

<160> NUMBER OF SEQ ID NOS: 28

<210> SEQ ID NO 1
<211> LENGTH: 9
<212> TYPE: PRT
<213> ORGANISM: Homo sapiens

<400> SEQUENCE: 1

Cys Thr Ile Gln Asn Cys Pro Leu Gly
1               5

<210> SEQ ID NO 2
<211> LENGTH: 8
<212> TYPE: PRT
<213> ORGANISM: artificial sequence
<220> FEATURE:
<221> NAME/KEY: MISC_FEATURE
<222> LOCATION: (1)..(1)
<223> OTHER INFORMATION: Xaa is Butyryl-Tyr(Me)
<220> FEATURE:
<221> NAME/KEY: MISC_FEATURE
<222> LOCATION: (8)..(8)
<223> OTHER INFORMATION: Xaa is Gly-NH2
<220> FEATURE:
<223> OTHER INFORMATION: Synthetic construct

<400> SEQUENCE: 2

Xaa Ile Gln Asn Cys Pro Leu Xaa
1               5

<210> SEQ ID NO 3
<211> LENGTH: 20
<212> TYPE: DNA
<213> ORGANISM: artificial sequence
<220> FEATURE:
<223> OTHER INFORMATION: PCR sense primer for amplification of Lpl gene

<400> SEQUENCE: 3
ggcatacagg tgcaattcca                                              20

<210> SEQ ID NO 4
<211> LENGTH: 22
<212> TYPE: DNA
<213> ORGANISM: artificial sequence
<220> FEATURE:
<223> OTHER INFORMATION: PCR anti-sense primer for amplification of Lpl
      gene

<400> SEQUENCE: 4
cgtcgaactt ggacagatcc tt                                           22

<210> SEQ ID NO 5
<211> LENGTH: 21
<212> TYPE: DNA
<213> ORGANISM: artificial sequence
<220> FEATURE:
<223> OTHER INFORMATION: PCR sense primer for amplification of Acaca
      gene

<400> SEQUENCE: 5
acctcaacca ctacggcatg a                                            21

<210> SEQ ID NO 6
<211> LENGTH: 19
<212> TYPE: DNA
<213> ORGANISM: artificial sequence
<220> FEATURE:
<223> OTHER INFORMATION: PCRanti-sense primer for amplification of Acaca gene

<400> SEQUENCE: 6
aggtggtgtg aaggcgttg                                        19

<210> SEQ ID NO 7
<211> LENGTH: 22
<212> TYPE: DNA
<213> ORGANISM: artificial sequence
<220> FEATURE:
<223> OTHER INFORMATION: PCR sense primer for amplification of Fasn gene

<400> SEQUENCE: 7
ggacatggtc acagacgatg ac                                    22

<210> SEQ ID NO 8
<211> LENGTH: 22
<212> TYPE: DNA
<213> ORGANISM: artificial sequence
<220> FEATURE:
<223> OTHER INFORMATION: PCR anti-sense primer for amplification of Fasn
      gene

<400> SEQUENCE: 8
cgtcgaactt ggacagatcc tt                                    22

<210> SEQ ID NO 9
<211> LENGTH: 21
<212> TYPE: DNA
<213> ORGANISM: artificial sequence
<220> FEATURE:
<223> OTHER INFORMATION: PCR sense primer for amplification of Dgat1
      gene

<400> SEQUENCE: 9
gttcagctca gacagcggtt t                                     21

<210> SEQ ID NO 10
<211> LENGTH: 20
<212> TYPE: DNA
<213> ORGANISM: artificial sequence
<220> FEATURE:
<223> OTHER INFORMATION: PCR anti-sense primer for amplification of
      Dgat1

<400> SEQUENCE: 10
catcaccacg caccaattca                                       20

<210> SEQ ID NO 11
<211> LENGTH: 20
<212> TYPE: DNA
<213> ORGANISM: artificial sequence
<220> FEATURE:
<223> OTHER INFORMATION: PCR sense primer for amplification of Pnpla2
      gene

<400> SEQUENCE: 11
ggccatgatg gtgccctata                                       20

<210> SEQ ID NO 12
<211> LENGTH: 19
<212> TYPE: DNA
<213> ORGANISM: artificial sequence
<220> FEATURE:
<223> OTHER INFORMATION: PCR anti-sense primer for amplification of
      Pnpla2 gene

<400> SEQUENCE: 12
ccaacaagcg gatggtgaa            19

<210> SEQ ID NO 13
<211> LENGTH: 21
<212> TYPE: DNA
<213> ORGANISM: artificial sequence
<220> FEATURE:
<223> OTHER INFORMATION: PCR sense primer for amplification of Hsl gene

<400> SEQUENCE: 13
ccccgagatg tcacagtcaa t            21

<210> SEQ ID NO 14
<211> LENGTH: 19
<212> TYPE: DNA
<213> ORGANISM: artificial sequence
<220> FEATURE:
<223> OTHER INFORMATION: PCR anti-sense primer for amplification of Hsl
      gene

<400> SEQUENCE: 14
gaattcccgg atcgcagaa            19

<210> SEQ ID NO 15
<211> LENGTH: 14
<212> TYPE: DNA
<213> ORGANISM: artificial sequence
<220> FEATURE:
<223> OTHER INFORMATION: PCR sense primer for amplification of
      PPAR-alpha gene

<400> SEQUENCE: 15
gtccctcgga gagg            14

<210> SEQ ID NO 16
<211> LENGTH: 14
<212> TYPE: DNA
<213> ORGANISM: artificial sequence
<220> FEATURE:
<223> OTHER INFORMATION: PCR anti-sense primer for amplification of
      PPAR-alpha gene

<400> SEQUENCE: 16
ggaagctgga gaga            14

<210> SEQ ID NO 17
<211> LENGTH: 19
<212> TYPE: DNA
<213> ORGANISM: artificial sequence
<220> FEATURE:
<223> OTHER INFORMATION: PCR sense primer for amplification of Acox1
      gene

<400> SEQUENCE: 17
cgaccttgtt cgggcaagt            19

<210> SEQ ID NO 18
<211> LENGTH: 24
<212> TYPE: DNA
<213> ORGANISM: artificial sequence
<220> FEATURE:
<223> OTHER INFORMATION: PCR anti-sense primer for amplification of
      Acox1 gene

<400> SEQUENCE: 18
tgagaagacc ttaacgacca cgta                                          24

<210> SEQ ID NO 19
<211> LENGTH: 21
<212> TYPE: DNA
<213> ORGANISM: artificial sequence
<220> FEATURE:
<223> OTHER INFORMATION: PCR sense primer for amplification of Ehhadh
      gene

<400> SEQUENCE: 19
tccctggctt tctacgttcc t                                             21

<210> SEQ ID NO 20
<211> LENGTH: 18
<212> TYPE: DNA
<213> ORGANISM: artificial sequence
<220> FEATURE:
<223> OTHER INFORMATION: PCR anti-sense primer for amplification of
      Ehhadh gene

<400> SEQUENCE: 20
gatggtgcgc tgctcgat                                                 18

<210> SEQ ID NO 21
<211> LENGTH: 19
<212> TYPE: DNA
<213> ORGANISM: artificial sequence
<220> FEATURE:
<223> OTHER INFORMATION: PCR sense primer for amplification of Acadm
      gene

<400> SEQUENCE: 21
cgccggaaca cgtactttg                                                19

<210> SEQ ID NO 22
<211> LENGTH: 21
<212> TYPE: DNA
<213> ORGANISM: artificial sequence
<220> FEATURE:
<223> OTHER INFORMATION: PCR anti-sense primer for amplification of
      Acadm gene

<400> SEQUENCE: 22
cgagctggtt ggcaatatct c                                             21

<210> SEQ ID NO 23
<211> LENGTH: 20
<212> TYPE: DNA
<213> ORGANISM: artificial sequence
<220> FEATURE:
<223> OTHER INFORMATION: PCR sense primer for amplification of Ucp3 gene

<400> SEQUENCE: 23
ggacagcagc ctgtattgca                                               20

<210> SEQ ID NO 24
<211> LENGTH: 21
<212> TYPE: DNA
<213> ORGANISM: artificial sequence
<220> FEATURE:
<223> OTHER INFORMATION: PCR anti-sense primer for amplification of Ucp3
      gene

<400> SEQUENCE: 24
gggttgcact tcggaagttg t                                             21

```
<210> SEQ ID NO 25
<211> LENGTH: 21
<212> TYPE: DNA
<213> ORGANISM: artificial sequence
<220> FEATURE:
<223> OTHER INFORMATION: PCR sense primer for amplification of Scd1 gene

<400> SEQUENCE: 25
ccgtggcttt ttcttctctc a                                              21

<210> SEQ ID NO 26
<211> LENGTH: 20
<212> TYPE: DNA
<213> ORGANISM: artificial sequence
<220> FEATURE:
<223> OTHER INFORMATION: PCR non-sense primer for amplification of Scd1
      gene

<400> SEQUENCE: 26
ctttccgccc ttctctttga                                                20

<210> SEQ ID NO 27
<211> LENGTH: 17
<212> TYPE: DNA
<213> ORGANISM: artificial sequence
<220> FEATURE:
<223> OTHER INFORMATION: PCR sense primer for amplification of oxt gene

<400> SEQUENCE: 27
cgcctgcgac cctgagt                                                   17

<210> SEQ ID NO 28
<211> LENGTH: 22
<212> TYPE: DNA
<213> ORGANISM: artificial sequence
<220> FEATURE:
<223> OTHER INFORMATION: PCR anti-sense primer for amplification of oxt
      gene

<400> SEQUENCE: 28
aaggaagcgc cctaaaggta tc                                             22
```